US008359692B2

(12) United States Patent
Brewer

(10) Patent No.: US 8,359,692 B2
(45) Date of Patent: Jan. 29, 2013

(54) DENTAL CLEANING DEVICE

(76) Inventor: Gerald K. Brewer, Los Angeles, CA (US)

( * ) Notice: Subject to any disclaimer, the term of this patent is extended or adjusted under 35 U.S.C. 154(b) by 631 days.

(21) Appl. No.: 12/555,662

(22) Filed: Sep. 8, 2009

(65) Prior Publication Data

US 2010/0062397 A1 Mar. 11, 2010

Related U.S. Application Data

(60) Provisional application No. 61/095,219, filed on Sep. 8, 2008.

(51) Int. Cl.
*A46B 9/04* (2006.01)
*A61C 17/22* (2006.01)

(52) U.S. Cl. ............ 15/22.1; 15/167.2; 15/201; 433/216

(58) Field of Classification Search .................. 15/22.1, 15/167.2, 201; 601/139–142; 433/216; *A46B 9/04; A46C 17/22*
See application file for complete search history.

(56) References Cited

U.S. PATENT DOCUMENTS

| 1,894,509 | A | * | 1/1933 | Booth | 15/201 |
| 2,935,755 | A | * | 5/1960 | Leira et al. | 15/167.1 |
| 3,504,692 | A | | 4/1970 | Goldstein | |
| 3,630,294 | A | | 12/1971 | Bouyoucos et al. | |
| 3,874,084 | A | | 4/1975 | Cole | |
| 4,011,616 | A | | 3/1977 | Kennedy | |
| 4,224,710 | A | | 9/1980 | Solow | |
| 4,346,492 | A | * | 8/1982 | Solow | 15/22.1 |
| 4,795,347 | A | | 1/1989 | Maurer | |
| 5,072,471 | A | | 12/1991 | Isler | |
| 5,177,827 | A | * | 1/1993 | Ellison | 15/22.1 |
| 5,184,368 | A | * | 2/1993 | Holland | 15/167.1 |
| 5,259,083 | A | * | 11/1993 | Stansbury, Jr. | 15/22.1 |
| 5,497,526 | A | * | 3/1996 | Klinkhammer | 15/167.2 |
| 5,524,319 | A | * | 6/1996 | Avidor | 15/167.1 |
| 5,615,443 | A | * | 4/1997 | Lai | 15/167.2 |
| 5,669,097 | A | * | 9/1997 | Klinkhammer | 15/167.1 |
| RE35,941 | E | * | 11/1998 | Stansbury, Jr. | 15/22.2 |
| 6,353,956 | B1 | * | 3/2002 | Berge | 15/22.1 |
| 6,389,636 | B1 | * | 5/2002 | Savill | 15/167.1 |
| 7,036,179 | B1 | | 5/2006 | Weihrauch | |
| 7,082,638 | B2 | * | 8/2006 | Koh | 15/22.1 |
| 7,334,283 | B2 | * | 2/2008 | Kunita et al. | 15/28 |
| 7,600,288 | B1 | * | 10/2009 | Givonetti | 15/167.1 |
| 7,743,452 | B1 | * | 6/2010 | Tcholakov | 15/201 |
| 7,832,043 | B1 | * | 11/2010 | Feldman | 15/28 |
| 2004/0074035 | A1 | * | 4/2004 | Huang | 15/167.2 |
| 2004/0194238 | A1 | * | 10/2004 | Letendre | 15/22.2 |
| 2008/0216257 | A1 | * | 9/2008 | Ahadpour et al. | 15/22.1 |
| 2009/0044360 | A1 | * | 2/2009 | Davidson et al. | 15/167.2 |
| 2009/0229062 | A1 | * | 9/2009 | Filby | 15/22.1 |
| 2011/0113576 | A1 | * | 5/2011 | Yankell | 15/167.2 |

* cited by examiner

*Primary Examiner* — Robyn Doan
*Assistant Examiner* — Tatiana Nobrega

(57) ABSTRACT

Powered toothbrush systems that provide improved bristle positioning and bristle contact with tooth surfaces that reduce the time and effort required for effective brushing. Some embodiments use alternating or oscillating pneumatic pressure and suction to move a tooth brush head. Various configuration of the brush head provide different areas of coverage ranging from individual tooth to quarter mouth (U-cross section), to half (U-cross section or H-cross section) or whole mouth (U-cross section or H-cross section) coverage. Some embodiments include flexible fingers and/or bladders to keep the bristle tips properly engaged with the teeth and gums, providing bristle contact over a wide variety of malocclusion. The shape of the brush heads adapts to conform closely to the shape of the user's dental arch and to any malocclusion that may be present. The power toothbrush automatically generates motion of the brush head that simulates the "Modified Bass Method" of brushing.

21 Claims, 20 Drawing Sheets

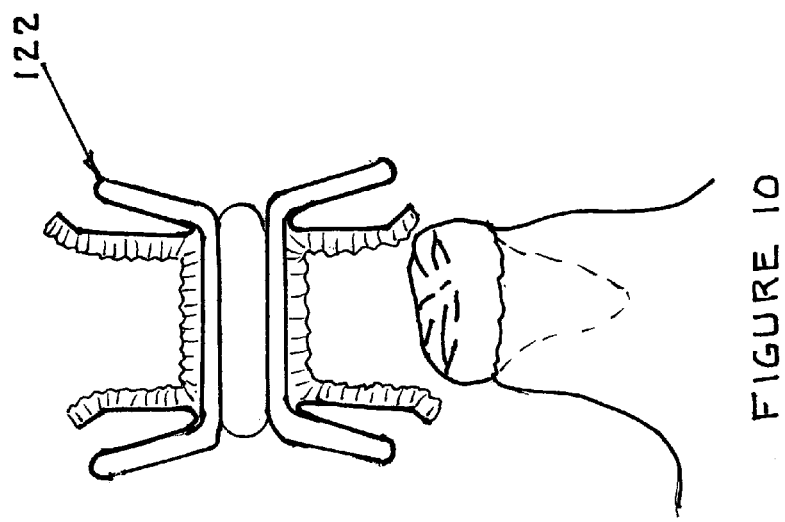

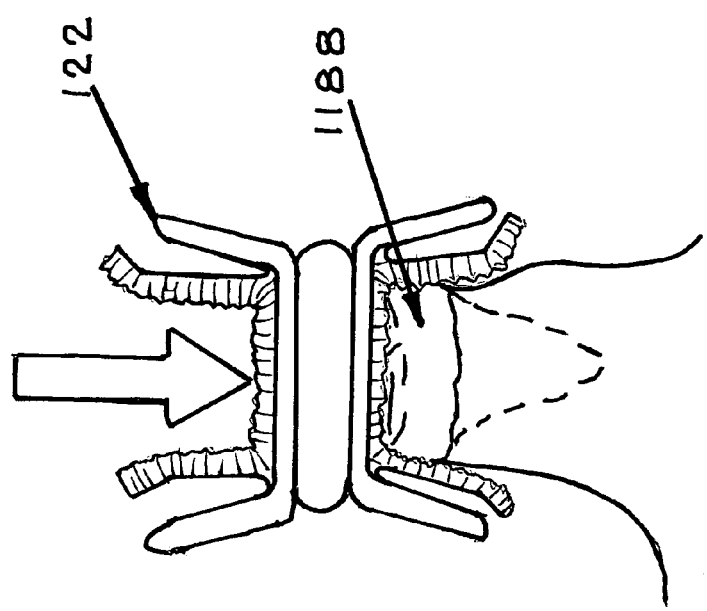

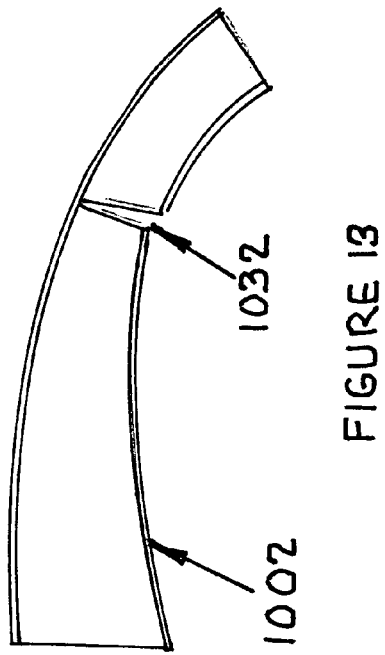
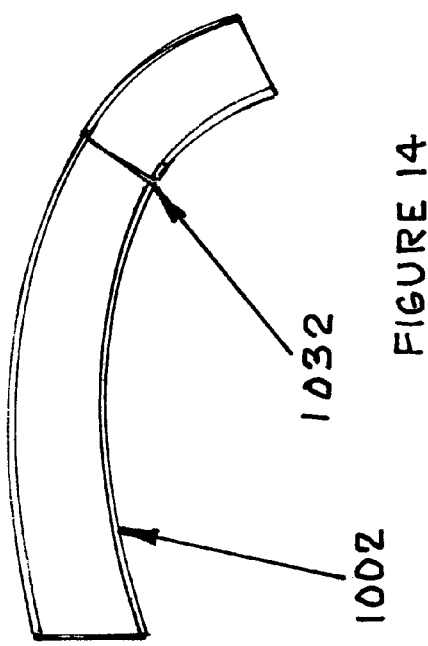
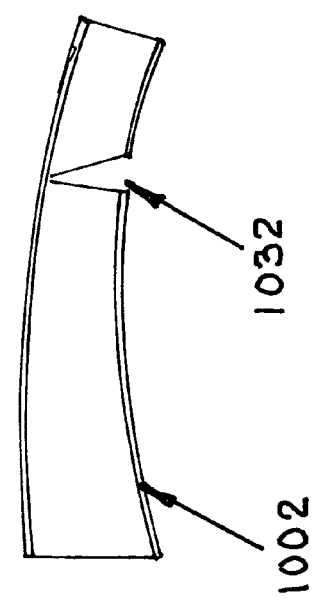

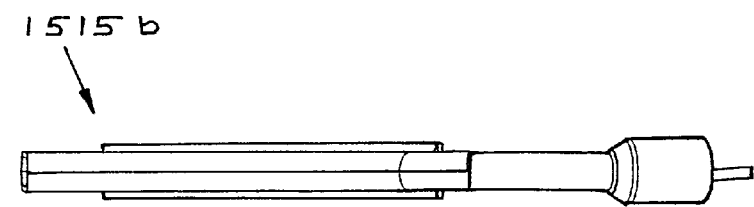
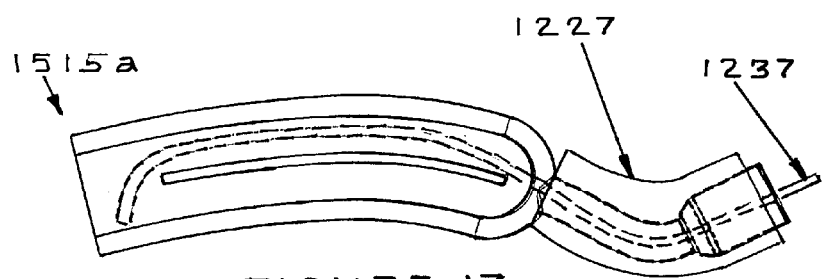
FIGURE 17
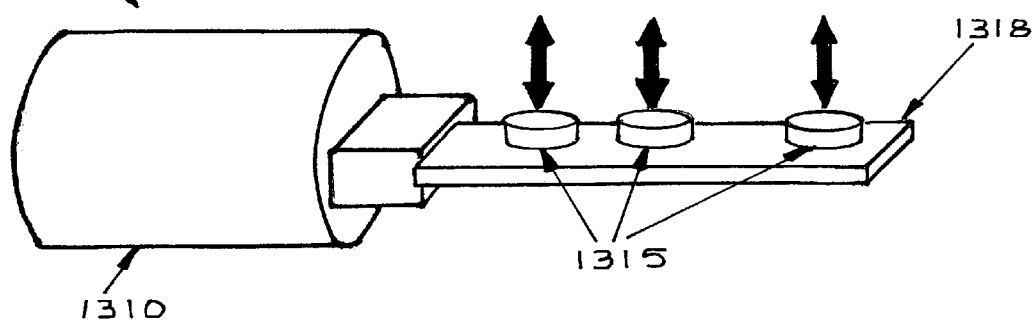
FIGURE 18

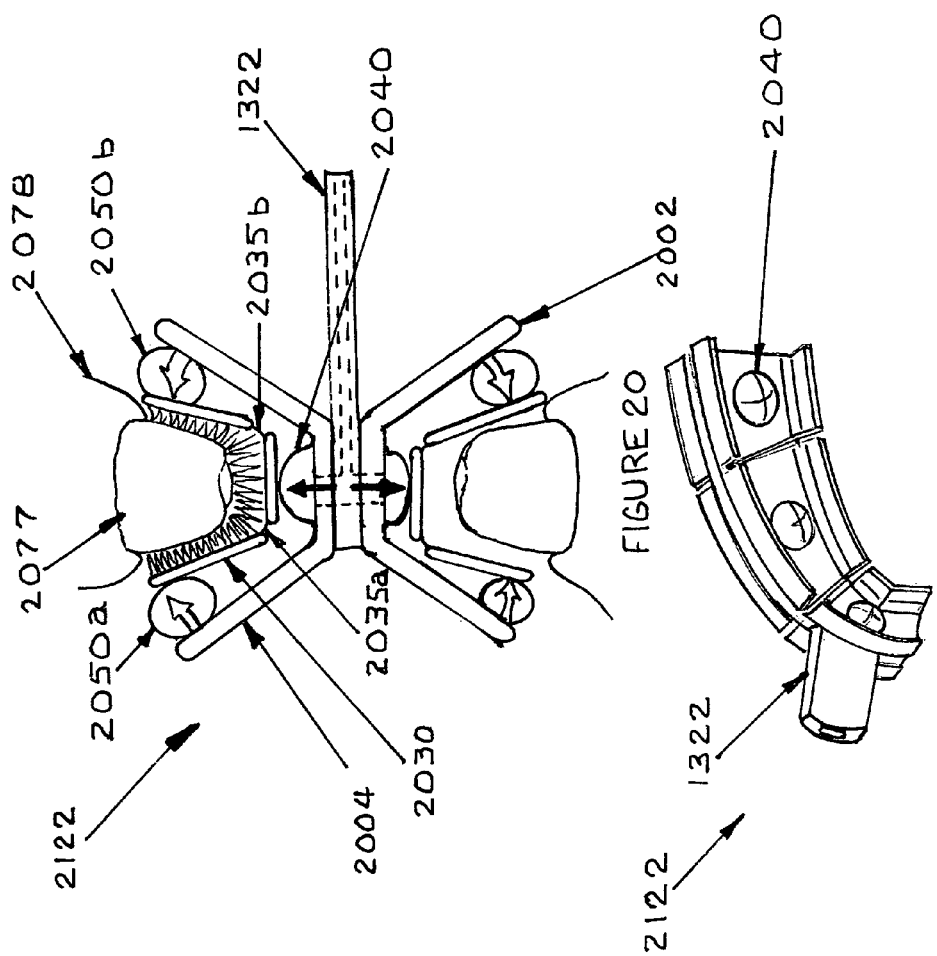

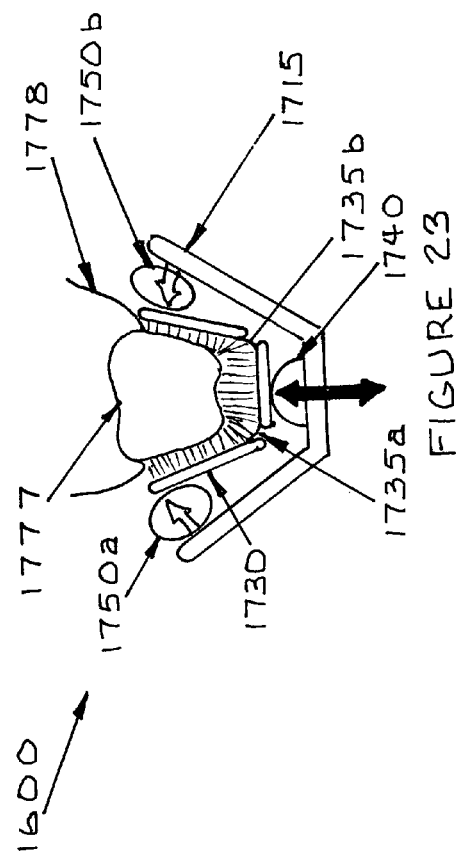
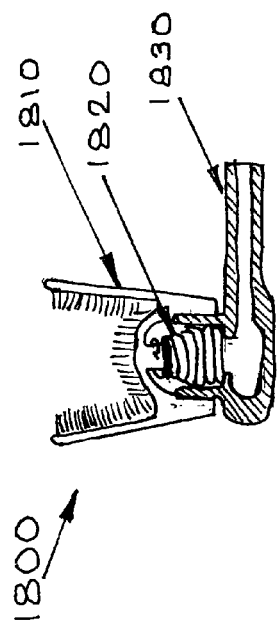
FIGURE 23
FIGURE 24

DENTAL CLEANING DEVICE

RELATED APPLICATION

This application claims the benefit of U.S. provisional patent application Ser. No. 61/095,219 entitled "Improved Dental Cleaning Device," filed on Sep. 8, 2008, which is incorporated herein by reference in its entirety.

FIELD OF THE INVENTION

The present invention generally relates to the field of dental cleaning and relates to a powered tooth brush that provides a brushing motion that produces improved cleaning of teeth.

BACKGROUND

Cleaning one's teeth is a necessary, yet time consuming chore necessary for good oral health. Various manual and powered dental cleaning products exist for the removal of dental plaque from the teeth. Most manual and power toothbrushes require two or more minutes of use in order to effectively remove plaque buildup. However, studies have shown the average person only brushes for a mere thirty-seven seconds. Furthermore, nearly eighty-seven percent of the population does not floss daily, which may lead to additional plaque buildup between teeth that can result in poor oral health.

Power toothbrushes have been shown by clinical studies to more effectively remove plaque. But, less than 30 percent of the population of the United States uses a power toothbrush. The effectiveness of power toothbrushes is also very technique dependent. Small brushing heads on typical toothbrushes require precision positioning for the bristles to contact the proper locations on the teeth. Poor technique may result in tooth surfaces being cleaned in a non-uniform fashion, which may lead to plaque buildup that is even more difficult to remove during subsequent cleanings. Poor brushing techniques may also lead to other oral health problems, such as soft-tissue abrasion, gingival recession, cervical wear (wear occurring at the neck of the tooth), and dentinal hypersensitivity.

SUMMARY

Systems for improved dental care devices are provided that address the shortcomings of conventional dental care devices. Embodiments provide a power toothbrush with improved bristle positioning and bristle contact with tooth surfaces that reduce the time and effort required for effective brushing. Some embodiments use alternating or oscillating pneumatic pressure and suction to move a tooth brush head. The size of the brush head can vary, providing different areas of coverage with individual coverage areas ranging from individual tooth to quarter mouth (U-cross section), to half (U-cross section or H-cross section) or whole mouth (U-cross section or H-cross section) coverage. Some embodiments include flexible fingers and/or bladders (air or fluid) to keep the bristle tips properly engaged with the teeth and gums, providing bristle contact over a wide variety of malocclusion. The shape of the brush heads adapts to conform closely to the shape of the user's dental arch and to any malocclusion that may be present. The power toothbrush automatically generates motion of the brush head that simulates the "Modified Bass Method" of brushing that is recommended by dental professionals as being most effective for removal of dental plaque.

According an embodiment of the present invention, a power toothbrush is provided. The power toothbrush includes a handle portion, a pneumatic pump disposed within the handle portion, and a brush head coupled to the handle portion. The brush head includes a first dental arch that includes a first set of brush pads for simultaneously cleaning multiple tooth surfaces of a first set of teeth. The first set of teeth includes at least one tooth from the maxillary dental arch of a user. The brush head also includes a second dental arch that includes a second set of brush pads for simultaneously cleaning multiple tooth surfaces of a second set of teeth. The second set of teeth oppose the first set of teeth. The second set of teeth includes at least one tooth from the mandibular dental arch of a user. The power toothbrush further includes an inflatable bladder disposed between the first and second dental arches. The inflatable bladder is in fluid communication with the pneumatic device. The pneumatic pump providing pressure to inflate the bladder and suction to deflate the bladder. The inflation of the bladder causes the first dental arch and the second dental arch to move apart and deflation of the bladder cause the first and second dental arches to move together, moving the first set of brush pads in an upward and downward motion along the multiple tooth surfaces of the first second set of teeth and moving the second set of brush pads in an upward and downward motion along the tooth surfaces of the second set of teeth.

According another embodiment of the present invention, a power toothbrush is provided that includes a handle portion and a brush head coupled to the handle portion. The brush head includes an upper brush component for simultaneously cleaning multiple tooth surfaces of a first set of teeth. The first set of teeth including at least one tooth from the maxillary dental arch of a user. The brush head also includes a lower brush component for simultaneously cleaning multiple tooth surfaces of a second set of teeth. The second set of teeth opposes the first set of teeth and includes at least one tooth from the mandibular dental arch of a user. The brush head also includes a driving mechanism for alternating between driving the first dental arch and the second dental arch together and driving the first dental arch and the second dental arch apart.

According to yet another embodiment, a method for brushing using a power toothbrush that includes a brush head that includes a first dental arch and a second dental arch with a driving mechanism disposed between the first and second dental arches is provided. The method includes fitting the brush head to the mouth of a user such that the first dental arch conforms to a first set of teeth of the maxillary arch of the user and the second dental arch conforms to a second set of teeth of the mandibular arch of the user where the second set of teeth opposing the first set of teeth. The method also includes alternating between driving the first dental arch and the second dental arch together and driving the first dental arch and the second dental arch apart.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 10 illustrates a brush head of a power toothbrush; and

FIG. 11 illustrates the brush head of FIG. 23 engaged with a set of teeth

FIG. 12 illustrates a view of a dental arch for use with a brush head according to an embodiment;

FIG. 13 illustrates another view of the dental arch of FIG. 12;

FIG. 14 illustrates yet another view of a dental arch of FIG. 12;

FIG. 17 illustrates a pair of inflatable bladders that may be used with a brush head according to an embodiment;

FIG. 18 illustrates a power toothbrush according to an embodiment;

FIG. 20 illustrates a brush head for a power toothbrush according to an embodiment;

FIG. 21 illustrates another view of the brush head illustrated in FIG. 20;

FIG. 23 illustrates a cross-sectional view of the brush head of FIG. 22;

FIG. 24 illustrates a piston style actuator according to an embodiment;

DETAILED DESCRIPTION

Figure 1:
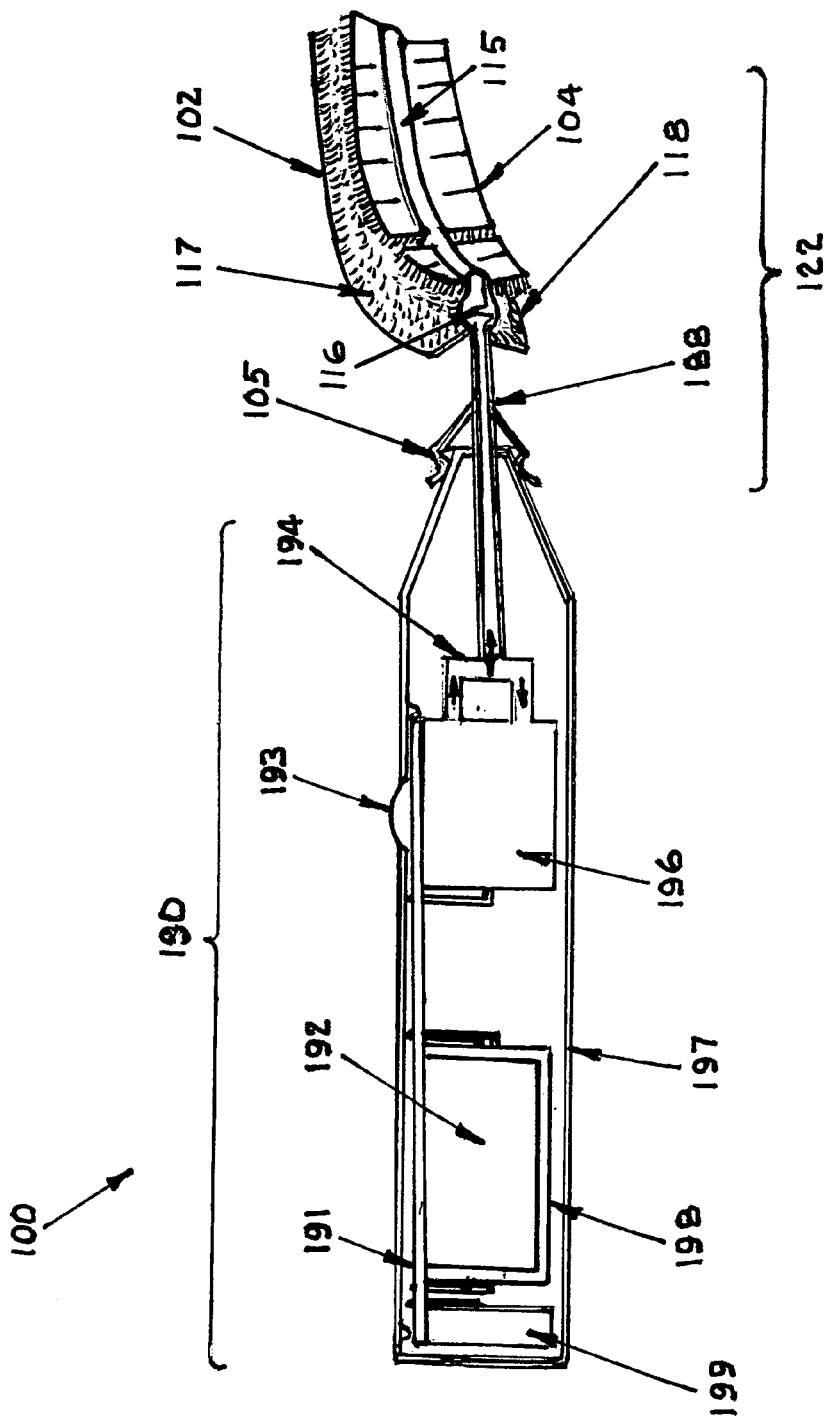
FIG. 1 illustrates a power toothbrush according to one embodiment.

Systems and methods for a powered toothbrush are provided. Embodiments of the powered toothbrush can provide three key advantages over conventional tooth cleaning systems: compliance, conformity, and comfort. Compliance with a proper brushing regime includes two factors: technique and time. Many people do not execute a proper brushing technique, and even if the technique used were correct, the length of time that most people brush is far less than is recommended to effectively remove dental plaque. Both of these factors can result in missed dental plaque that can lead to poor oral health.

Embodiments of the powered toothbrush enable users to easily execute a compliant brushing technique in a much shorter period of time than is required using conventional tooth brushing systems and methods. The time and dexterity required for effective brushing is also reduced, and the effectiveness of tooth brushing can also be increased for persons having limited dexterity, such as the elderly, the handicapped, and small children. Embodiments of the present invention also provide brush heads that decrease the amount of time required to execute a compliant brushing regime by brushing multiple teeth simultaneously. For example some embodiments include brush heads that can brush all of the teeth in the mouth at once, half of the teeth in the mouth at once (all of the mandibular arch of teeth, all of the maxillary arch of teeth, or one half of the teeth of the mandibular arch and on half of the teeth of an opposing half of the maxillary arch simultaneously). Other configurations are also possible based upon the disclosure provided below.

Embodiments of the powered toothbrush provide effective cleaning of the teeth by providing the benefits of the "Bass Method" and the "Modified Bass Method" of brushing. These techniques are preferred by many dental professionals as being most effective for removing bacterial plaque removal adjacent to and directly beneath the gingival margin. Removal of dental plaque from the gingival margin provides a significant contribution to controlling gingival and periodontal disease. In the Bass Method, a manual toothbrush with a flat brushing plane and rounded nylon filaments is directed toward the gums at approximately a forty-five degree angle and an up and down motion is used to clean the teeth. The Modified Bass Method adds a slight circular motion to the up and down motion of the Bass Method. While the Bass Method of brushing is quite effective at cleaning the teeth and removing plaque, people often find the technique too difficult to execute correctly. Therefore, some dental professionals recommend the Modified Bass Method over the Bass Method of brushing. The Modified Bass Method is believed by some dental professionals to be more easily accomplished using a manual toothbrush, but the Bass Method provides more effective interproximal cleaning. Since relatively few people floss regularly, deep interproximal cleaning may significantly reduce the accumulation of calculus on the teeth, resulting in improved oral health. Embodiments of the powered toothbrush automatically move the brush heads to mimic the Bass Method of cleaning, enabling users to benefit from the more effective cleaning of the Bass Method without being limited by the manual dexterity of the users. Embodiments of the powered toothbrush provide the effective cleaning of the tooth surfaces and interproximal areas while removing the burden of mastering and executing challenging brushing techniques.

The powered toothbrush also provides conformity. People have a wide variety of dental arch shapes and sizes as well as a variety of tooth widths. Furthermore, the position of teeth can vary widely due to malocclusion where teeth are out of alignment. Embodiments of the powered toothbrush include adjustable brush heads that enable the brush head to conform to the specific parameters of users' mouths regardless of the size and shape of the users' dental arches, the users' tooth widths, and any malocclusion or misalignment of the users' teeth. Embodiments of the powered toothbrush provide improved bristle positioning that result in improved contact of the bristles with the tooth surfaces to provide more uniform cleaning of the teeth.

The powered toothbrush also provides a comfortable brushing experience. Users are not likely to use a system that is not comfortable to use. The brush heads of the power toothbrush system are formed from flexible materials that adjust to the shape of the user's mouth, and include thinner softer bristles that conventional toothbrush systems that are less likely to irritate sensitive teeth and/or gums.

FIG. 1 illustrates a power toothbrush 100 have a multi-tooth and/or multi-dental arch brush head according to one embodiment. The most common method of removing dental plaque is to generate a shearing force by the movement of toothbrush filaments over the exterior surfaces of the teeth. According to some embodiments, the power toothbrush 100 is configured to generate brush motions that mimic the brush motions of the Bass Method of brushing recommended by dental professionals.

The power toothbrush 100 includes a pneumatic system for conversion of electrical energy to filament motion. The power toothbrush 100 includes brush head that includes a driving mechanism, such as bladder 115, disposed between an upper brush component and a lower brush component. The upper brush component includes dental arch 102 and brush pad 117, and lower brush component includes dental arch 102 and brush pad 118. The driving mechanism alternatively drives the dental arches 102 and 104 apart and drives the dental arches 102 and 104 together to create a brushing motion. According to other embodiments, other driving mechanisms can be used, such as a driving a double bladder or a bladder having multiple chambers, a bladder in the form of a plurality of inflatable actuator domes, or other mechanical mechanisms, such as a motor with wobble weights to induce motion into the brush plates.

The power toothbrush 100 includes a pneumatic device to provide alternating or oscillating pneumatic pressure, such as a miniature piston air compressor 196, an air delivery system coupled to the miniature piston air compressor 196, and a flexible, elastic bladder 115 in fluid communication with air compressor 196 via manifold 194. The air compressor resides in handle portion 190 of the power toothbrush, and bladder 115 is layered between the mandibular arch (dental arch 102) and the maxillary arch (dental arch 104) of brush head 122. Air delivery manifold 194 connects the air compressor 196 to the bladder via coupling 188. Coupling 188 provides an air conduit from the air compressor 196 to bladder 115 According to some embodiments, pneumatic system is closed, except for a small amount of air intake used to make up for air leakage from the system. Additional details describing the interaction of the air compressor 196 and the bladder 115 are provided below with respect to FIGS. 15 and 16. According to some alternative embodiments, the pneumatic system is not closed, but instead, includes at least one pressure relief valve for releasing pressure from the system.

Dental arch 102 and dental arch 104 are J-shaped arches that enables right or left sagittal plane brushing of the mandibular dental arch and maxillary dental arch simultaneously (both the upper and lower teeth on one side of the mouth). Brush head 122 can be used to brush either side of the mouth. For example, a user can simply flip the brush over to brush the teeth on the other side of the mouth. According to some embodiments, dental arches 102 and 104 are U-shaped arches that enable brushing of the full mandibular dental arch and maxillary dental arches. According to some embodiments, dental arches 102 and 104 include soft tips along the edges of the dental arches that massage the user's gum line while the brush head 122 is cleaning the teeth.

Handle portion 190 also includes a switch 193 that enables a user to power on or power off power toothbrush 100. Carrier 192 is an internal structure for holding rechargeable battery 109 in place within handle housing 197. According to some embodiments, battery 198 is recharged using an external power source via charging coil 199. In some embodiments, charging coil 199 receives power from a docking station that holds power toothbrush 100 while the toothbrush not in use. According to other embodiments, charging coil 199 includes a plug interface that enables power toothbrush 100 to be plugged into mains power. Some embodiments may use disposable batteries, yet other embodiments may be powered by a high energy capacitor. Charge and pump control 191 controls the charging of battery 198 and routes power from battery 198 to pump 196.

Inflation and deflation of air bladder 115 is accomplished by alternatively applying pressure and suction to air bladder 115 by pump 196 via pneumatic manifold 194. According to some embodiments, a bladder in the form of one or more dome-shaped activators is used instead of a single large air bladder, such as air bladder 115. A detailed description of an embodiment using dome-shaped activators is described below with respect to FIG. 18.

Brush pad 117 is coupled to dental arch 102, and brush pad 118 is coupled to dental arch 104. According to some embodiments, the bristles of brush pads 117 and 118 are set at a forty-five degree angle to the surface of the teeth, the brush angle recommended in the Bass Method and Modified Bass Method.

Oscillation of air source pressure—switching between pressure and suction—rapidly inflates and deflates bladder 115 to drive the brush head 122 up and down relative to the surface of the teeth to create the brushing motion of power toothbrush 100. Bladder 115 is disposed between dental arches 102 and 104, and pumping air into the bladder 115 causes the bladder to inflate, which causes dental arches 102 and 104 to move apart from one another. Removing air from the bladder 115 causes the bladder to deflate, which causes dental arches 102 and 104 to move back toward one another. As air bladder 115 is alternatively inflated and deflated by pump 196 via pneumatic manifold 194, the dental arches 102 and 104 move apart in an upward and downward motion that causes brush pads 117 and 118 along the tooth surface.

The up and down motion created by the inflation and deflation of the bladder 115 results in a motion that mimics the brushing motions of the Bass Method. According to some embodiments, the inflation and deflation of the bladder 115 also impart a side-to-side motion to the dental arches, mimicking the semi-circular brushing motion of the Modified Bass Method. Thus, the powered toothbrush automatically provides a compliant brushing technique by mimicking the brushing motions of the Bass Method or the Modified Bass Method recommended by dental professionals without requiring that the user master complex brushing motion.

Bite restrictor 116 prevents air bladder 115 from being crushed if a user bites down on brush head 122. According to some embodiments, bladder 115 also includes an internal rib or ribs to prevent the walls of the bladder from being entirely collapsed due bite pressure being applied to the brush head 122. One benefit of using a single large bladder between the dental arches is that regardless of whether there is a "rake" in a user's bite (i.e., an imbalance in the bite pressure), the bite pressure is equalized across the dental arches by the bladder. For example, a user might exert a higher bite pressure at the back of the mouth versus the front of the mouth. The pressure gradient to runs down the center of bladder 115, and the bite pressure exerted by the user is distributed by the bladder, enabling the power toothbrush to adapt to the variability and irregularities of the bite pressure exerted by users.

Quick disconnect coupling 105 enables brush connects brush head 122 to pneumatic manifold 194. Quick disconnect coupling 105 enables brush head 122 to be removed from the handle portion 190 that includes the power supply and other electronic components of the power toothbrush in order to clean or replace the brush head. For example, multiple users may share the same toothbrush base by decoupling their brush head 1100 from the toothbrush base or the brush head may be disposable. The quick disconnect coupling 105 may be allowed to rotate up to 360 degrees which will help assure a comfortable grip and a well positioned brush head.

Figure 2:
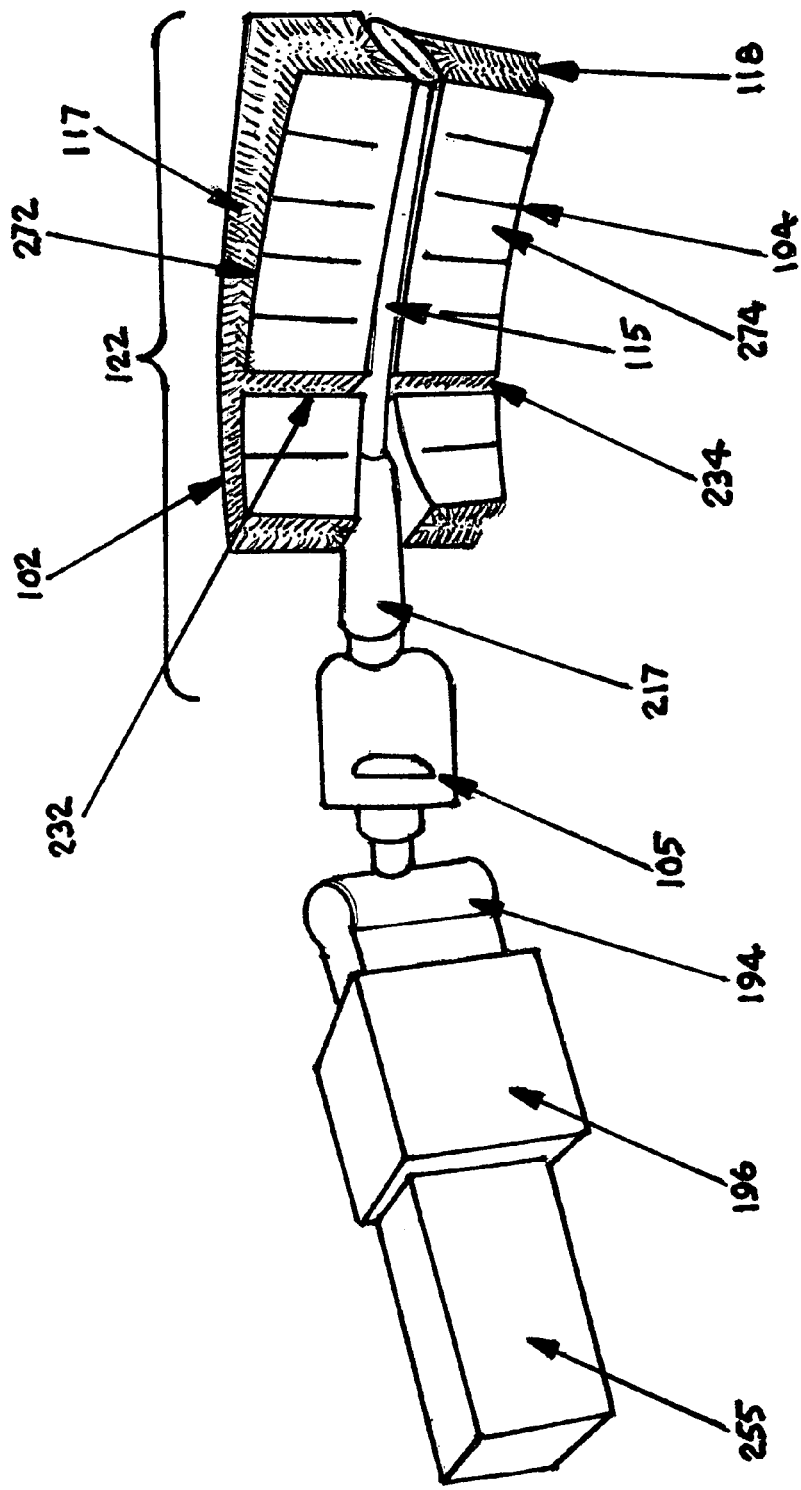
FIG. 2 illustrates a second view of the power toothbrush of FIG. 1.

FIG. 2 illustrates a view of power toothbrush 100 with the handle housing 197 removed to show the pump 196, motor 255, and pneumatic manifold 194. Motor 255 powers pump 254. Motor 255 receives power from battery 198 (see FIG. 1). Pneumatic manifold 194 couples to quick disconnect coupling 105.

According to some embodiments, protective sheath 217 and is bonded to the bladder 115. Sheath 217 help to prevent the neck of the bladder from becoming obstructed due to crushing or twisting of the neck of the bladder. According to some embodiments, sheath 217 is bonded to the upper and lower brush bases (dental arches) to promote free motion of the upper and lower portions of the brush while still being flexible enough to enable the brush to be positioned within the mouth.

Dental arch 102 includes a flex gap 232 and dental arch 104 includes flex gap 234 that allow the dental arches to bend longitudinally to conform with the arch of a user's teeth. The dental arches of people can vary significantly due to physical differences in the size and shape of individual mouths and due to tooth alignment problems (malocclusions). Therefore, according to some embodiments, dental arches 102 and 104 include at least one flex gap that enables the dental arches 102 and 104 to flex in order to adjust to the shape of a user's mouth. Flex gaps 232 and 234 provide significant longitudinal flex that allows the dental arches 102 and 104 to conform to the dental arches of the user while simultaneously providing brushing pressure to the teeth, even where there is wide variation in tooth width and alignment. According to some embodiments, the multiple flex gaps are incorporated into a dental arch to impart additional flexibility.

According to some embodiments, dental arches 102 and 104 are formed from a flexible material, such as, rubber or elastomer, which enables the dental arches to bend longitudinally. In some embodiments, dental arches 102 and 104 is formed from a heat setting elastomer, where the user heats the brush head in hot water to soften the elastomer of the dental arches. The user then places the heated brush head into their mouth to cause the softened dental arches to conform to the arch of the user's teeth. As the elastomer cools, the dental arches harden and retain the shape of the user's mouth.

According to some embodiments, the pneumatic system of the power toothbrush 100 is configured to not store a supply reservoir of air at a set pressure, unlike most conventional pneumatic systems. Instead, the air pressure in the system is dynamic. Each revolution of a piston of pump 196 has a compression stoke and a suction stroke. Flapper valves are used to direct air toward the bladder during the compression stroke to cause the bladder to inflate. The flapper valves also direct suction toward the bladder in an out-of-phase relationship. When both pressure and suction are joined in a common manifold, the resulting pressure differential inflates and deflates the bladders or bladders. The suction initiates a rapid deflation, more rapid than just letting the dental arches 102 and 104 fall as pressure decreases in the bladder or bladders.

According to some alternative embodiments, flapper values are not used to direct the flow of air and build pressure in the pneumatic system. Rather, a positive and negative cycling pressure scenarios is achieved in the bladder during each compressor revolution. With no flapper valves being used, the air from pump 196 is allowed to flow into or out of the bladder 115 as the piston of the pump 196 is pushing or pulling the air. In this embodiment the effect of keeping the dental arches in motion through either mechanical resonance or pneumatic volume tuning of the air cavity results in optimal motion. By selecting a drive frequency that is slightly higher frequency than the resonant frequency, when the whole brushing system is loaded the amplitude or apparent brushing power is increased. In this embodiment an increase in mass can actually be easier to move and stay in motion with less applied energy.

According to some alternative embodiments, various pump designs may be used to provide the pneumatic pressure to the pneumatic system of the powered toothbrush. For example, according to some embodiments a rotary motor with a pump section is used, while in other embodiments a linear motor with a cam, like a wobble weight, pushing on a bellows or a diaphragm is used to generate pneumatic pressure. In yet other embodiments, a linear motor with a piston pump is used. In some embodiments, a piezo device pushing a bellows may be used to generate pressure.

According to some embodiments, single crystal $Pb(Mg_{1/3}Nb_{2/3})_{1-x}Ti_xO_3$ (PMN-PT) or $Pb(Zn_{1/3}Nb_{2/3})_{1-x}Ti_xO_3$ PZN-PT is used as a non-electromagnetic motor. Such a motor is capable of moving very large displacements of 100's μm to either move a diaphragm to supply air or fluid for pneumatic operation of the brush head. Additionally, a single crystal motor of this type can be used to move a brush head by directly without the use of pneumatics. A motor of this type is capable of providing an ultrasonic vibration frequency in excess of 20 kHz.

Figure 26:
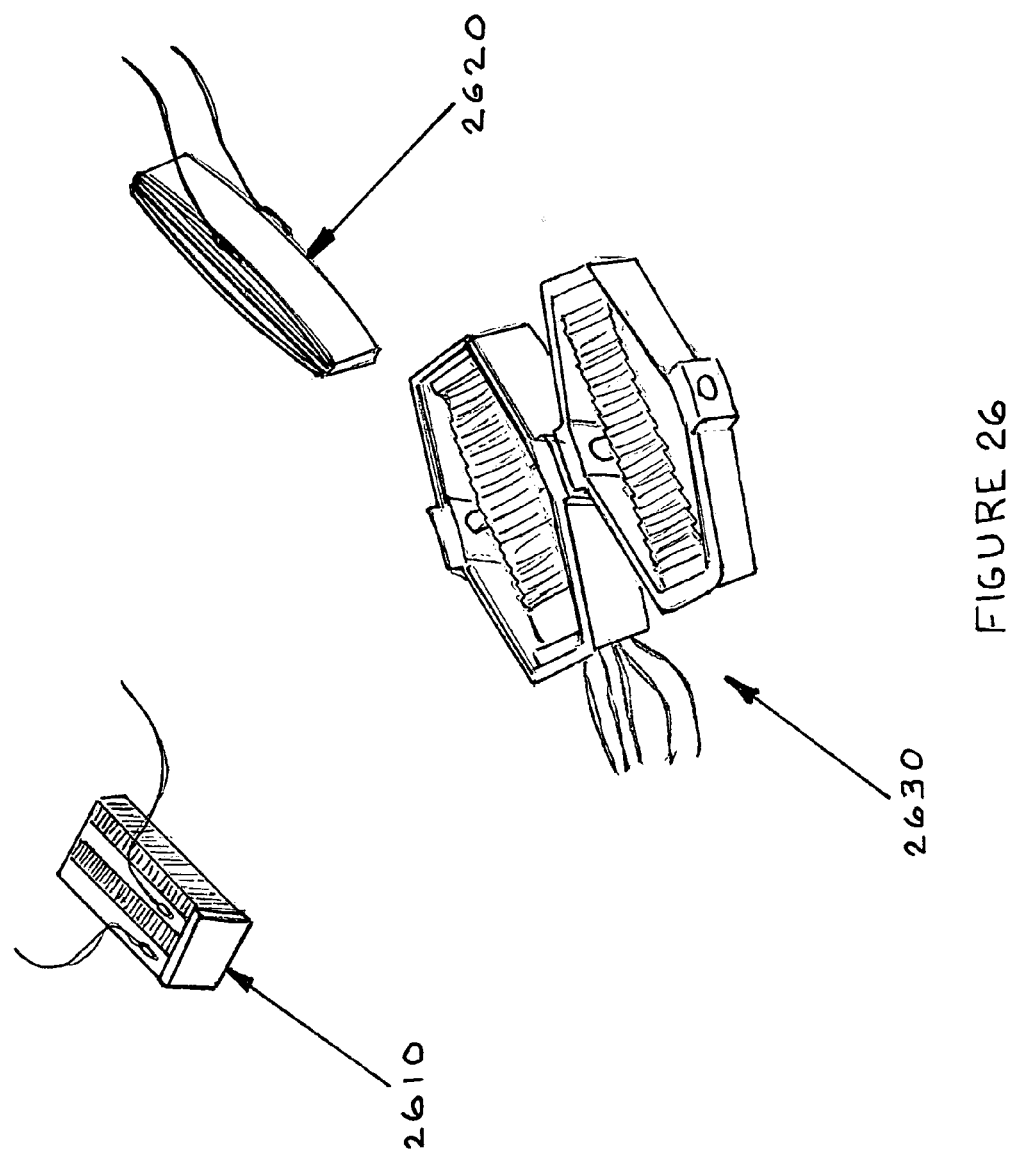
FIG. 26 illustrates several crystal actuators that may be used to drive a brush head according and embodiment.

According to some embodiments, crystal actuators may be used. FIG. 26 illustrates examples of three types of crystal actuators that are used in various embodiments: piston mode stacks 2610, transverse mode, low profile flex tensional actuators 2620, and high displacement flex tensional actuators using amplification frames 2630. The amplification frame can result in a larger motion than may be possible with a piezoelectric transducer or super crystal.

With a conventional electromagnetic motor, the brush displacement will likely be reduced at higher frequency. When using a piezo or single crystal, the displacement can be smaller yet, but with the higher frequency, dental plaque removal effects may be enhanced. With a conventional motor, the brush displacement will likely be less at higher frequency because moving large masses generally results in lower mechanical resonant frequencies. However, higher frequencies may produce higher velocity bristle tip action, so that short bristles, similar to those in the preferred embodiment (typically 1 mm to <5 mm) may be used.

Figure 3:
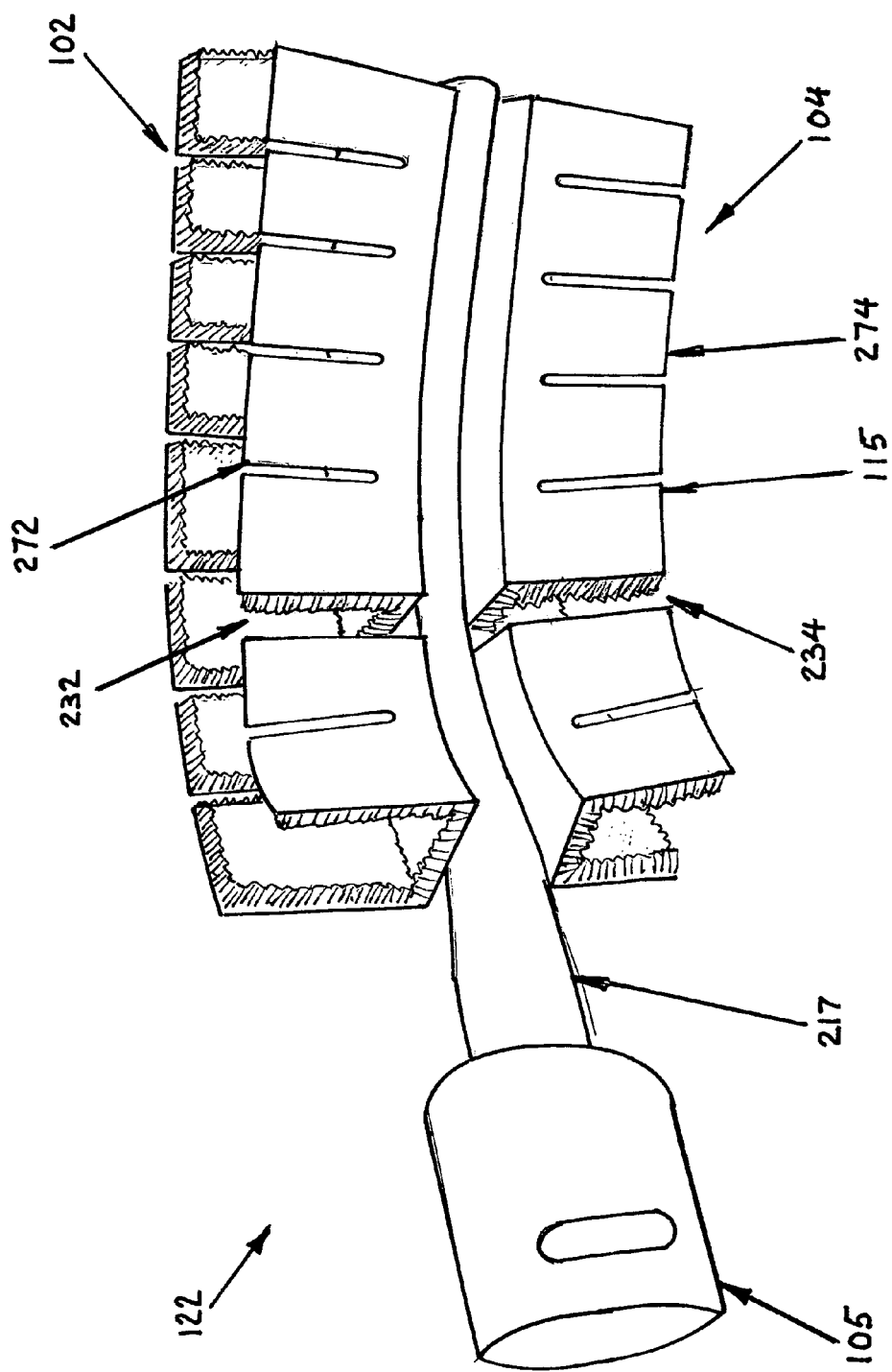
FIG. 3 illustrates the brush head of the power toothbrush of FIG. 2.

FIG. 3 provides an illustration of brush head 122 decoupled from handle portion 190 of power toothbrush 100. As described above, quick disconnect coupling 105 enables the brush head 122 to be disconnected from the handle portion 190 for cleaning or replacement.

Figure 4:
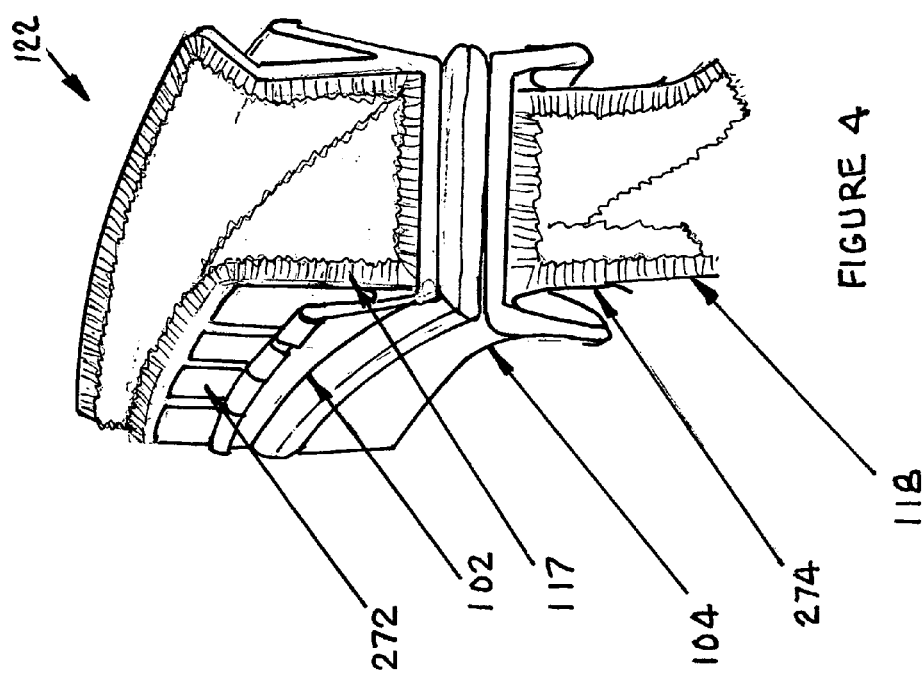
FIG. 4 illustrates a cross-sectional view of the brush head of FIG. 3.

FIG. 4 illustrates a cross-section of a brush head 122 according to an embodiment. FIG. 4 illustrates how flexible fingers 272 and 274 hold the brush pads in place. Flexible fingers 272 are coupled to dental arch 102 and hold brush pad 117 in place and provide pressure to brush pad 117 so that a cleaning surface of the brush pad 117 contacts the tooth surfaces of a user's tooth inserted into the tooth channel of the dental arch. Similarly, flexible fingers 274 are couple to dental arch 104 and hold brush pad 118 in place and provide pressure to brush pad 118 so that a cleaning surface of brush pad 118 contacts tooth surfaces of a user's tooth inserted into the tooth channel of the dental arch 104. The flexible fingers 272 and 274 provide a predictable spring force.

Figure 5:
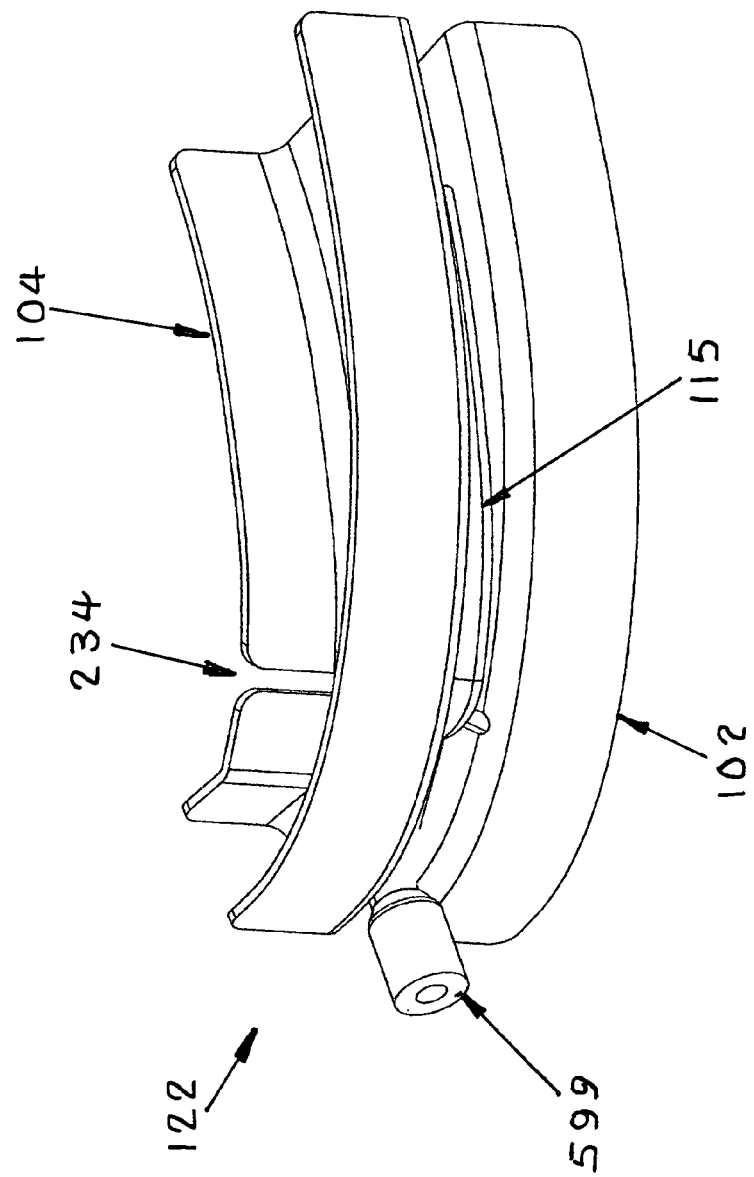
FIG. 5 illustrates a brush head that includes upper and lower dental arches that may be used with the power toothbrush according to an embodiment.
Figure 6:
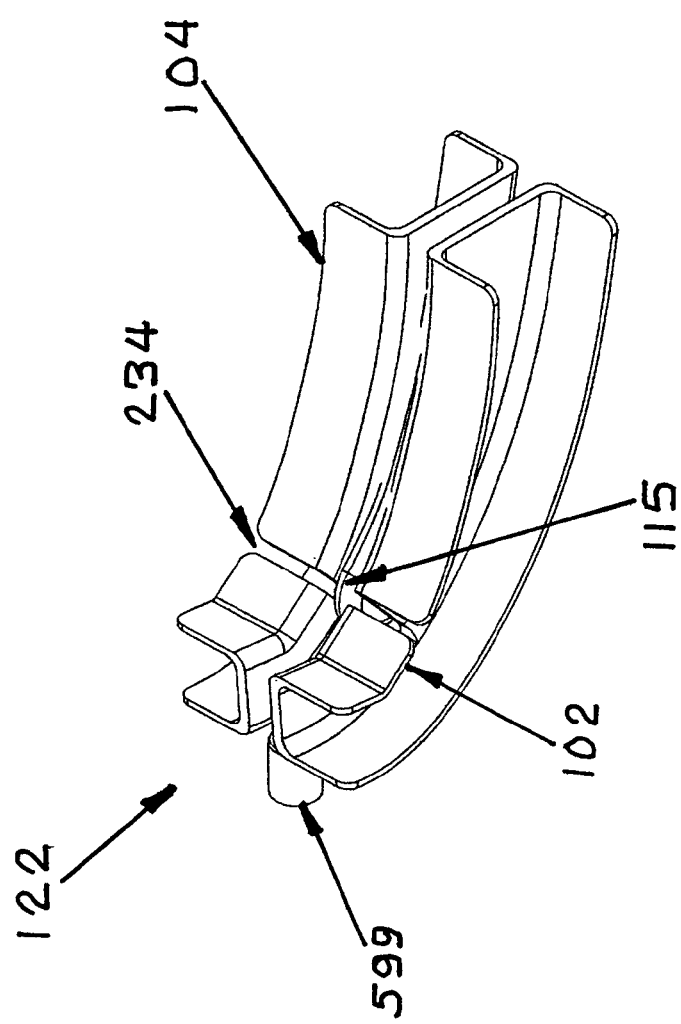
FIG. 6 illustrates another view of the brush head of FIG. 5 according to an embodiment.
Figure 7:
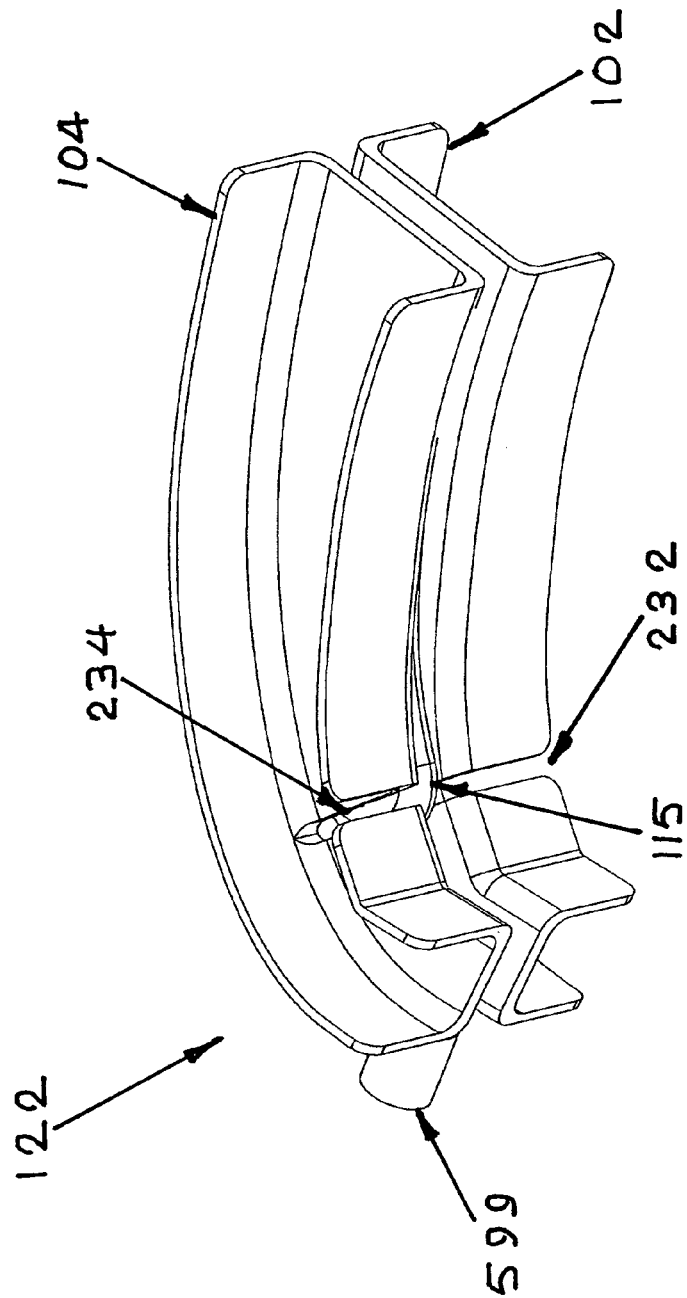
FIG. 7 illustrates another view of the brush head of FIG. 5 according to an embodiment.

FIGS. 5, 6, and 7 show an embodiment of brush head 122 from several different angles. Brush head 122 is illustrated with brush pads 117 and 118 and flexible fingers 272 and 274 removed to illustrate the shape of the dental arches 102 and 104. Sheath 217 has also been removed so that the neck 599 of bladder 115 is also visible in FIGS. 5, 6, and 7.

Figure 8:
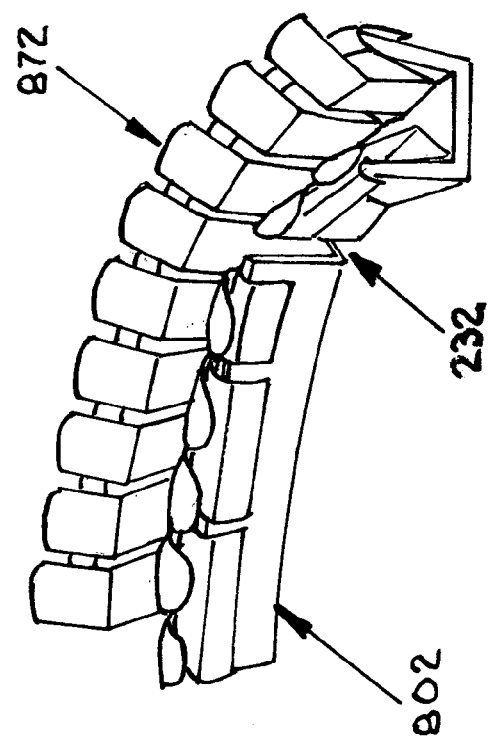
FIG. 8 illustrates a top view of a dental arch of a brush head according to an embodiment.

FIG. 8 illustrates a dental arch 802 similar to dental arches 102 and 104 described above and includes a set of flexible fingers 872 similar to flexible fingers 272 and 274 for holding brush pads (not shown) on the dental arch according to an embodiment. The brush pads, which are described in greater detail below, contact the tooth surfaces to clean the tooth surfaces and remove dental plaque. The flexible fingers help the brush pads to comply with malocclusions and/or other irregularities in the tooth alignment.

According to some embodiments, the flexible fingers comprise metal, plastic, an elastomeric material, or a combination thereof that provides a predictable spring force. According to some embodiments, the flexible fingers 404 are silver plated to help to reduce microbial action on the brush head or are coated with or formed from a material having antimicrobial properties.

Brush pads or bristle pads for cleaning the tooth surfaces, such as brush pads 117 and 118, are attached to the flexible fingers 872, and the flexible fingers apply pressure on the brush pads that cause a cleaning surface of the brush pad to contact the surface of a user's teeth. The brush pads can conform to the tooth surfaces even where malocclusions are present. Because the pressure from the flexible fingers 872 helps to keep the cleaning surface of the brush pads in contact with the surface of the teeth, the length of the bristles used on the brush pads can be much shorter than the bristle length that may have been required if the bristles alone were used to conform to the dental arch of the user's teeth. According to an embodiment, the brush pads include bristles that are set perpendicular to acute to the surface of the teeth with the distal end of the bristles being directed toward the gingival sulcus in order to remove bacterial plaque adjacent to and directly beneath the gingival margin. According to a preferred embodiment, the bristles are angled at approximately 45 degrees to the surface of the teeth.

According to some embodiments, the brush pads are attached to the flexible fingers using an adhesive. According other embodiments, the brush pads include a rigid backing that may be snapped or locked into place on the dental arches 102 and 104. According to some embodiments, the brush pads may be removable and replaceable to allow a user to replace the brush pads without having to replace the entire brush head. Various techniques may be used to snap or lock the brush pads into place. According to some embodiments, heat staking or ultrasonic staking may be used to attach the brush pads to the dental arches. For example, the brush pads may have one or more posts extending from a rigid backing that are fused to a dental arch. According to other embodiments, stretch snaps may be used to attach the brush pads to the dental arches. For example, the brush pads may include one or more rubber tips that are stretched, inserted through an opening in the dental arch and released, and the rubber tip unstretches and expands wide enough that the tip cannot escape from the opening and holds the brush pad in place. According to another embodiment, a "pop bead" or pop beads may be used to hold the brush pads in place. The pop beads comprise a molded round feature that is molded onto the rigid backer of the brush pad and is snapped into a corresponding opening on the dental arch. The pop beads enable the rigid backing of the brush pads to rotate around the axis of the pop bead, which can help to align the brush heads with the teeth during use. According to yet another embodiment, ultrasonic welds may be used to affix the brush heads to the dental arch. For example, the brush pad may be formed from a plastic material that is compatible with the plastic of the dental arches, and the brush pads may be ultrasonically welded to the dental arches.

According to an embodiment, the bristle diameter of the bristles on the brush pads is approximately 0.001 to 0.003 inch. Soft small diameter bristles of $\leq 0.005$ inch diameter aid in deep penetration to hard to clean areas of the mouth, such as interproximal gaps and occlusal grooves. The smaller the diameter of the bristles, the shorter a tuft may be and maintain relative stiffness of the bristles. According to some embodiments, the bristle diameters are approximately 0.003 to 0.005 inch with a length of approximately 1 to 5 mm. The brush pads should provide nearly full coverage of the tooth surfaces. Thus, even minimal movement of the brush head in the mouth should provide full cleaning of the tooth surfaces including interproximal areas and occlusal grooves.

In a conventional toothbrush design, nylon bristles are typically attached using a staple set, molding, or fusing technique. Conventional staple set bristling technology can result in brushes with lower bristle density than may be achieved using the bristle pads disclosed herein. Thus, conventional brush heads using staple set technology may result in less plaque removal due to the lower bristle density.

According to some embodiments, the brush pads used by the power toothbrush are fabricated using a textile fabrication process. According to some embodiments, the bristles are manufactured as part of the bristle pad fabric, while in yet other embodiments, the bristles may be attached to the surface of the fabric or inserted through the fabric. According to various embodiments, the fabric comprises various types of materials, such as a film (e.g., Mylar), a polymer or elastomer. Flexible fingers 872 enable the bristles to be flat while providing efficacious brushing pressure to the tooth surfaces. According to some embodiments, inflatable bladders are included behind the flexible fingers 872 or inflatable bladders are used in place of flexible fingers 872 to apply pressure to the brush pad. These bladders, when inflated, push the bristles of the brush pad against the teeth so that the brush pad conforms to the teeth.

According to some embodiments, a combination of conventional bristling and bristled fabric is used. A combination of conventional bristling with the bristled fabric provides a very high bristle density that may provide improved removal of dental plaque. According to some embodiments, groupings of bristle strands are coupled to the bristled fabric of the brush pads, and in some embodiments, the lengths of the bristles included in the bristle strands may vary to shape the bristle strands.

The brush pads used of the power toothbrush described here may require significantly lower efficacious brushing pressures to be applied to the tooth surfaces during brushing. Conventional tooth brushing methods require higher levels of pressure to be applied to the tooth surfaces. For example, the efficacious brushing bristle pressure for a sweeping sonic brush is approximately 75 to 150 grams of pressure, with a pressure of approximately 125 grams typically being applied to the tooth surfaces of one to two teeth. The bristles of the sweeping sonic brush often vary between 0.005 and 0.007 inches in diameter and are typically comprised of Nylon 6-6 (e.g., DUPONT TYNEX filaments or equivalent) and have a bristle length of approximately 10 mm. The typical brushing pressure for another type of conventional brush, oscillating scrubbers is approximately 148 to 200 grams of pressure with the pressure typically being applied to the one tooth. The typical brushing pressure for a manual brush is approximately 350 to 750 grams with a nominal pressure of approximately 500 grams. Most manual brushes include 0.007 to 0.009 inch Nylon 6-6 bristles (e.g., DUPONT TYNEX filaments or equivalent). Another manual brush made for brushing tender gums, includes 0.004 to 0.005 inch diameter Nylon bristles.

The flexible fingers 872 may be engineered to provide a wide range of brushing pressures. For example, according to a preferred embodiment, the pressure fingers 872 are engineered to provide approximately 26 grams of pressure to the tooth surfaces.

According to some embodiments, the flexible fingers 872 are made from plastic or metal, and the amount of pressure provided by the pressure fingers can be increased by making the material thicker. For example, according to an embodiment, the flexible fingers 872 are made of metal that is 0.003 inch thick in order to deliver about 26 grams force, thicker metal results in higher brushing pressure.

Figure 9:
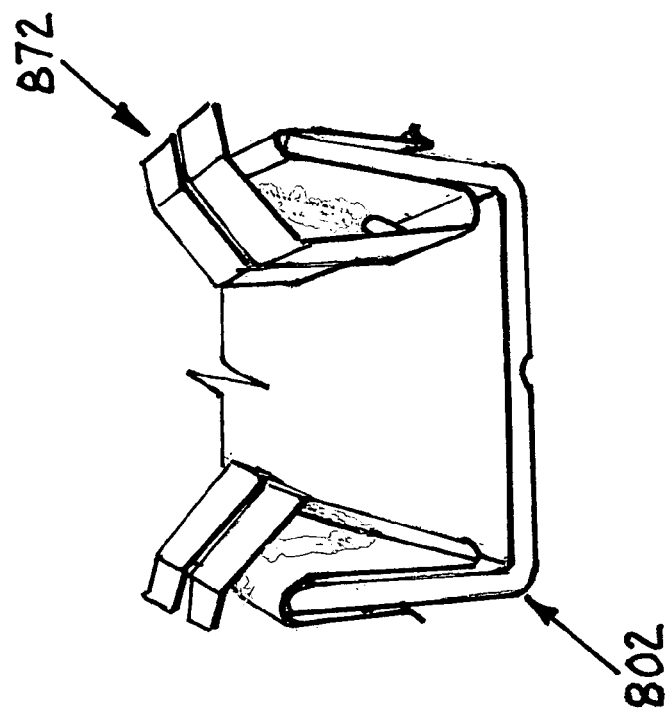
FIG. 9 illustrates a cross-sectional view of the dental arch of FIG. 8.

FIG. 9 illustrates a cross section of the brush head 800 of FIG. 8. The dental arch 802 includes U-shaped tooth channel. Dental arch 802 could be paired with a second dental arch having a U-shaped tooth channel to create an H-shaped brush head similar to that illustrated in FIGS. 2 and 3 for brushing both upper and lower teeth simultaneously. The flexible fingers 804 clip onto the sides of the tooth channel and hold the brush pads into place and apply pressure to the brush pads so that a cleaning surface of the brush pads contact the tooth surfaces. The flexible fingers 872 can flex independently of one another, enabling the brush pads to come into contact with the tooth surfaces, even if significant malocclusion is present.

FIG. 10 illustrates brush head 122 prior to be fitted to a set of teeth to illustrate the function of the flexible fingers. Because the dental arch of the brush head has not yet been fitted to the teeth, the flexible fingers not compressed. An optimal finger compression is approximately 50% to 80%. The basic width variations of the dental arch and the flexible fingers could be adjusted to optimize the fit to as large a portion of the populous as possible. FIG. 11 illustrates the brush head 122 fitted to the teeth. In the embodiment illustrated in FIG. 24, the molar 1188 is approximately 10 mm in width. The flexible fingers achieve approximately 50% compression and provide approximately 26 grams of pressure per tooth surface.

FIGS. 12, 13, and 14 illustrate a dental arch 1002 that is similar in design to dental arches 102 and 104 described above. Dental arch 1002 includes a flex gap 1032 similar to flex gap 232 of dental arch 104 and flex gap 234 of dental arch 104. FIGS. 12, 13, and 14 illustrate the flexibility imparted to the dental arches of the brush heads by the flex gaps that enable the brush heads to conform to the users having differently shaped mouths and/or various malocclusions. FIG. 12 illustrates a top view of dental arch 1002 in a positive longitudinal flex position according to an embodiment. FIG. 13 illustrates a top view of dental arch 1002 in a neutral longitudinal flex position according to an embodiment. FIG. 14 illustrates a top view of dental arch 1002 in a negative longitudinal flex position according to an embodiment. Due to the flexibility of the dental arches and the flex in the flexible fingers that hold the brush pads in place, the bristles can be much shorter in length and yield a smaller brush head than is possible if the bristles provided the entire bristle tip fit to the mouth.

Figure 15:
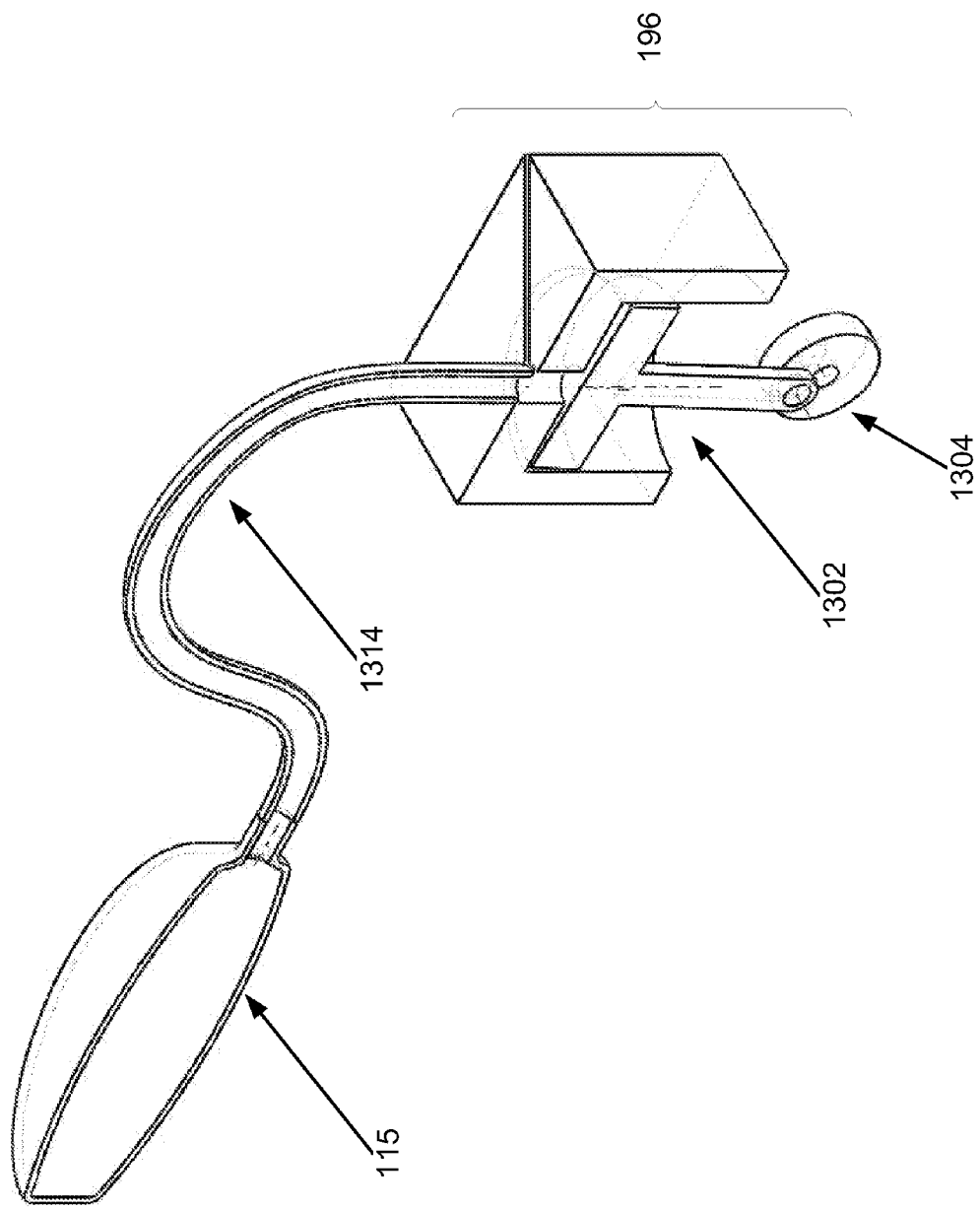
FIG. 15 illustrates a pump that may be used with the powered toothbrush system according to an embodiment.
Figure 16:
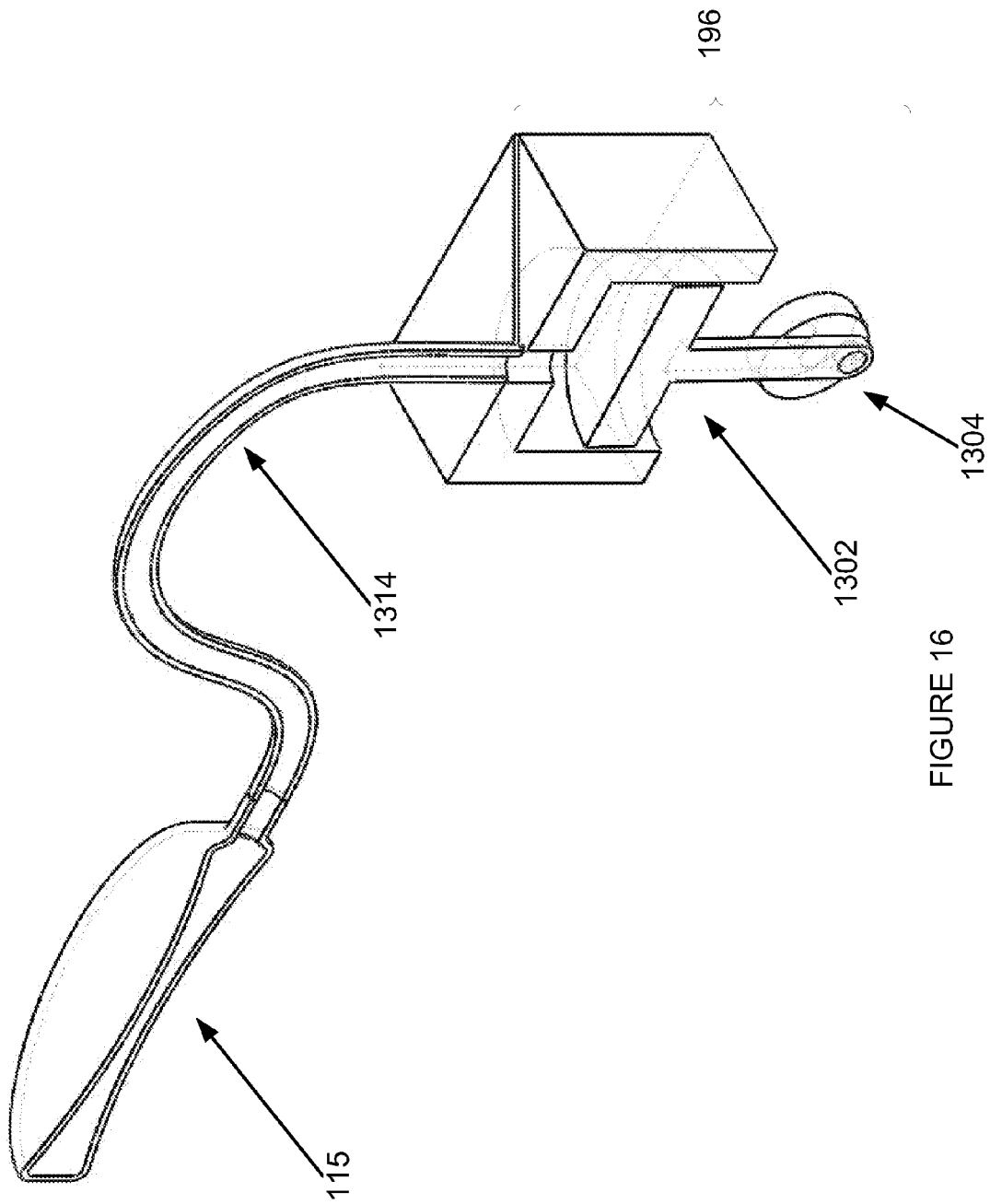
FIG. 16 illustrates a second view of a pump that may be used with the powered toothbrush system according to an embodiment.

FIGS. 15 and 16 illustrate an embodiment of a pump 196 for use in powered toothbrush 100 according to an embodiment. Pump 196 is in fluid communication with bladder 115 via a manifold 1314. Manifold 1314 may be similar to manifold 194 described above and provides an air-tight transport for air from the pump 196 to bladder 115. According to some embodiments, a pneumatic fluid may be used to inflate the bladder instead of air or another gas.

Piston 1302 is coupled to flywheel 1304. When flywheel 1304 rotates, piston 1302 is forced upward or downward. According to some embodiments, flywheel 1302 is driven by motor 255. When piston 1302 is forced upward, air is forced from pump 196 into manifold 194 and into bladder 115. When piston 1302 is forced downward, air is pulled from bladder 115 into the manifold 194 and into the pump 196.

Since bladder 115 is made of flexible, elastic material, bladder 115 tends to inflate and expand with positive internal pressure provided by pump 196, causing the surface of the bladder to be pushed away from a plane that is located through the center of the bladder. Bladder 115 tends to deflate and contract when negative internal pressure is applied by pump 196, causing the surface of the bladder to be drawn toward the central plane. The tooth contact elements, such as dental arches 102 and 104 including the flexible fingers 272 and 274 and the brush pads 117 and 118, are attached to bladder 115, and thus, share the motion of bladder. The location of the center plane of bladder 115 while included in a brush head being used for brushing depends on the orientation of the brush head with respect to the occlusal surfaces of the mandibular and maxillary teeth as well as the pressure being applied by the jaw muscles. As described above, a user may gently bite down on brush head 122 in order to cause the dental arches of the brush head to flex and conform to the shape of the user's dental arch.

Optimizing the displacement of the tooth cleaning members to achieve a desired brushing motion requires balancing of the dynamic behavior of the pneumatic components of the system, including factors such as the total air volume of the system, the pressure characteristics of the pump during each revolution, the mechanical characteristics of the bladder, and the flow performance of the air delivery passages (e.g., the manifold).

The speed of the compressor of pump 196 affects all of the above mentioned parameters. The metric for the speed of the compressor is revolutions per minute. According to an embodiment, a target speed of approximately 30 to 80 revolutions per second. According to some embodiments, a target speed of approximately 55 Hz may provide optimal results.

The mass of the moving components of the pneumatic system will affect the dynamic performance of the brush as the inertia loads the system. As the mass increases the force required to move it increases. According to Newton's law as it is commonly known, force F=ma, where a is the acceleration and m is the mass or inertia. By minimizing the mass of moving components, less force is required from the bladder to move the cleaning elements. The exception is when motion is near resonance. The flywheel effect can work to keep mass in motion.

Air in the system is driven from the compressor to the bladder and back again for each revolution of the compressor. All impediments to free air flow will create inefficiencies that result in lower dynamic performance. The size, shape, and materials of all interconnecting air passageways need to be optimized. As always this optimization will probably require tradeoffs in performance to gain the lowest cost and easiest to manufacture unit.

Optimizing the mass of the moving components and the size, shape, and materials of the interconnecting air passageways can result in a smaller compressor being required to effectively drive the brush head. A smaller compressor means that smaller batteries are required to power the compressor and that less space in handle portion 190 is required for the compressor and for the batteries. The size of the handle could be further optimized by using smaller batteries with a lower capacity that provides fewer brushings before requiring a recharge.

As stated above the compressor has a compression and decompression stroke for each revolution. According to some embodiments, the maximum positive pressure for the compression stroke falls in the range of 20 to 30 pounds per square inch (psi), and the maximum negative pressure is limited to an absolute vacuum of approximately −14.7 psi. According to some embodiments, the absolute vacuum is limited to approximately −6 to −9 psi. Thus, there is more pressure available on the compression stroke. However as the pressure in the system increases, the volume of air pushed out decreases according to the equation of state, $PV=mRT$. Due to this pressure difference, there is some optimal positive average pressure that results in maximum bladder deflection. According to some embodiments, a pressure control value is included in the pneumatic systems of the power toothbrush to release pressure if the pressure increases above the optimal positive average pressure. However, some positive pressure is desired to keep a slight inflation of the bladder to yield a comfortable feel in the mouth. This slight inflation enables oscillating motion with less energy consumed.

According to an embodiment, the volume of air displaced per stroke by the air compressor is balanced with the volume of the air delivery component and the volume of bladder 115. The total per revolution bladder deflection is directly related to the volume added per stroke on the positive pressure side plus the volume subtracted from the bladder on the negative pressure stroke. This volume change is also directly related to the average pressure in the bladder. As the average bladder pressure increases, the volume change (and correspondingly the tooth contact component displacement) in the bladder for any given compressor size will decrease.

The bite force applied to the tooth contact members adds to the average pressure in the bladder 115, which can negatively affect performance of the pneumatic system. According to some embodiments, the pneumatic system of the power toothbrush includes a pressure control value that releases pressure from the system to mitigate pressure imparted by the user's bite pressure. There are several valve implementations (i.e. duckbill, umbrella or flapper valves) that may be suitable for inclusion in a replacement brush head such as those used in the power toothbrush.

According to some embodiments, the shape and design of the brush head is optimized to control and direct the user's bite force to control how this bite force affects bladder 115. For example, bladder 115 could be formed and/or placed such that the much of the bladder action occurs at the outer edges of the occlusal surfaces of the teeth. The up and down cleaning motion imparted by the bladder could be augmented with a motion directing the tooth contact surfaces of the brush head into the gingival margins and the interproximal areas.

Attachment challenges, such as ease of replacement of the brush heads, the ability to adjust the brush orientation with respect to the handle portion 190, the air worthiness of the attached, and the size of the brush head all may impact the performance of the power toothbrush. Careful balancing of these parameters provides an optimal brushing motion that gives a user maximal benefit from using the power toothbrush.

FIG. 17 illustrates a pair of inflatable bladders 1515a and 1515b that are similar to bladder 115 that may be used with various embodiments of brush heads that described above. Air bladders 1515a and 1515b have a J-shape that conforms to the curvature of the dental arches used in the brush heads used for right or left sagittal plane brushing of the mandible and maxilla simultaneously. Air bladder 1515a includes an anti-twist stabilizer 1237 that provides torsion that keeps the brush head rotationally stable without reducing brush motion. Anti-twist stabilizer 1237 help to prevent air bladder 1515a from distorting out of shape due to the bite pressure and twisting exerted by a user on a brush head or from distorting out of shape when suction is applied to remove air from air bladder 1210 in order to move a set of dental arches of a brush head up and down. Protective sheath 1227 may be similar to protective sheath 217 and is bonded to the bladder to prevent the neck of the bladder. Sheath 1227 help to prevent the neck of the bladder from becoming obstructed due to crushing or twisting of the neck of the bladder. According to some embodiments, sheath 1227 is bonded to the upper and lower brush bases (dental arches) to promote free motion of the upper and lower portions of the brush while still being flexible enough to enable the brush to be positioned within the mouth. Bladder 1515b illustrates an example of the bladder with anti-twist stabilizer 1237 and sheath 1227 removed where the narrow neck of the bladder can be seen.

According to some embodiments, the air bladder is formed from a flexible and inflatable material, such as silicone rubber, thermoplastic elastomers (TPE) also referred to as thermoplastic rubber. Other flexible materials that can withstand repeated inflation and deflation may also be used. Air bladder 1210 may be formed by injection molding or via other methods known to the art. According to some embodiments, the walls of the inflatable bladder are rated less than 40 Shore A hardness and typically is less than 0.020 inch thick. According to a preferred embodiment, the walls of bladder 1210 are less than 0.008 inch thick. Bladders can also be constructed from mylar, PVC or other sheet material that is stretched to shape or bonded together using methods known in the arts.

FIG. 18 illustrates an alternative implementation of a power toothbrush 1300 that uses a driving mechanism that comprises a bladder in the form of a plurality of activation domes that move the move the bristle pads or bristle plates that come into contact with the tooth surfaces. The use of a bladder comprising a plurality of smaller more focused actuator domes can significantly reduce the volume of air or fluid needed to cause the bristle plate to rise and fall. As a result, a smaller pneumatic actuator may be required, thereby decreasing the overall size and weight of the device and increasing the portability of the device.

Power toothbrush 1300 includes handle portion 1310 that includes a battery, drive circuitry, a pneumatic pump, and a coupling to couple the handle portion 1310 to the brush head 1318. Brush head 1318 is shown as having a straight, non-curved shape in order to more clearly illustrate the function of the activation domes. The shape of the brush head can vary. In some embodiments, the activation domes are incorporated in full or partial mouth brush heads similar to those described above.

Brush head 1318 includes a plurality of activation domes 1315 for moving the bristle pads against the teeth rather than a large single bladder, such as bladder 115, used in the embodiments described above. The activation domes 1315 are formed from a flexible material, and positive pressure is applied by the pump, the domes inflate and when negative pressure (suction) is applied by the pump, the domes deflate.

Activation domes 1315 are composed of a flat material that enables the brush head to maintain a low side profile with minimal space between the upper and lower teeth of the user. Also, due to the rotational and mechanical vibration of most conventional power toothbrushes, many users find that sealing their lips while using the toothbrush is not easily accomplished. Sealing the lips prevents the loss of dental fluid while brushing.

Figure 19:
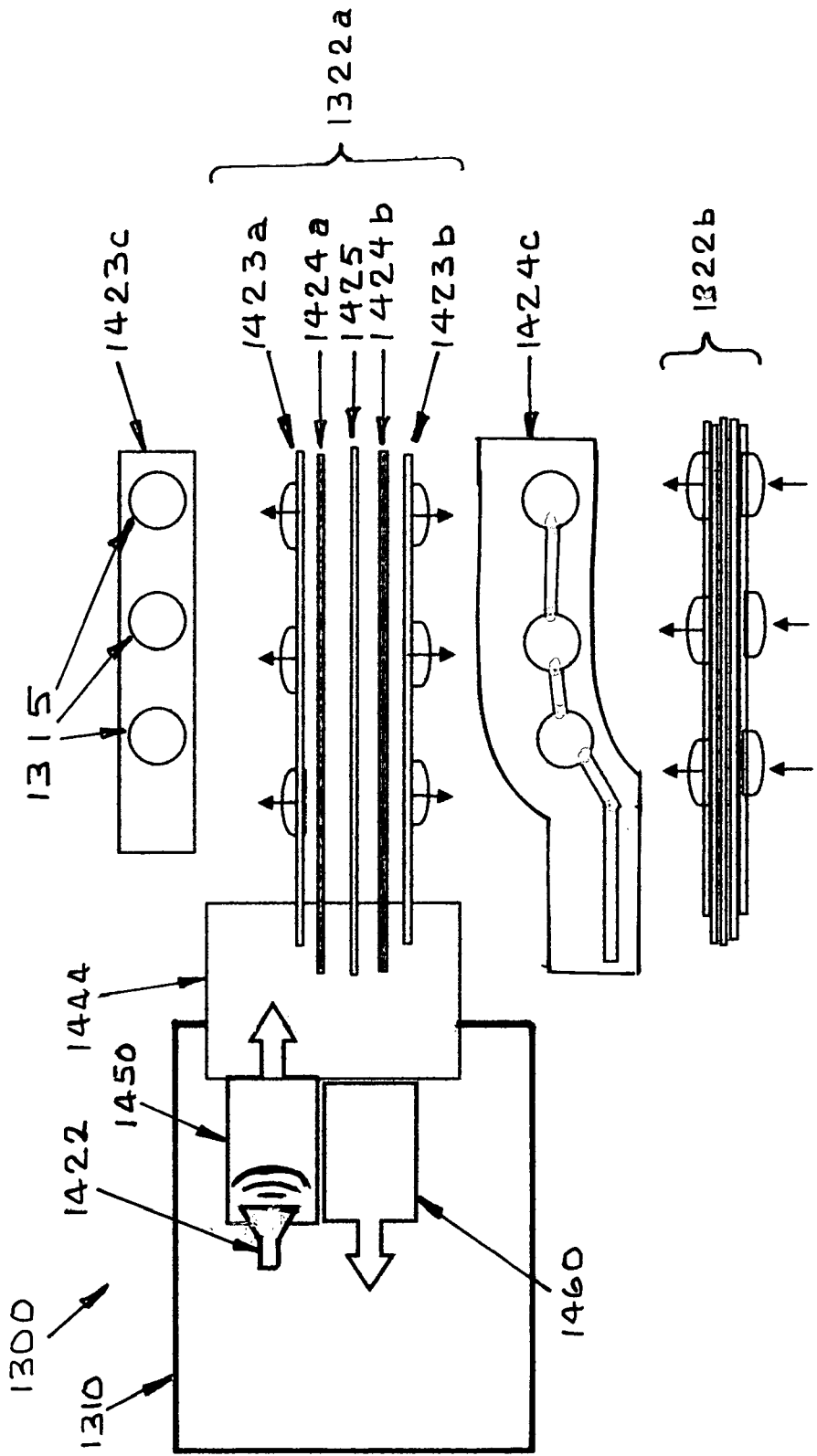
FIG. 19 illustrates the activation domes of the power toothbrush illustrated in FIG. 18 according to an embodiment.

FIG. 19 illustrates one possible configuration of a power toothbrush 1300 using a bladder in the form of a plurality of activation domes such as that described in FIG. 18 integrated into brush head 1322. The brush handle portion 1310 of power toothbrush 1300 includes a pump 1450 for applying positive pressure to the activation domes and a suction device 1460 for removing air from the activation domes. According to some embodiments, a single pneumatic pump is used to provide both pressure and suction.

Brush head 1322 include five layers. The five layers are shown separated in a first view 1322a and laminated together in a second view 1322b. Layers 1423a and 1423b are mirror images of one another, and layers 1424a and 1424b are also mirror images of one another. Layers 1423a and 1423b comprise a thin flexible membrane with a plurality of formed domes. A top view 1423c of layer 1423a illustrates the placement of the plurality of formed domes in the embodiment. Layers 1424a and 1424b act as a manifold 1444 that includes straight and round openings, through which air or fluid can pass to act upon the dome shaped membranes of layers 1423a and 1423b. A top view 1424c illustrates the layout of the straight and round openings that allow air or fluid to pass and act upon the dome shaped membranes. According to some embodiments, air flow through the manifold layers 1423a and 1423b is controlled and balanced by incorporating holes of various sizes to balance the pressure needed to inflate the activation domes throughout layers 1423a and 1423b. By balancing pressure at each of the activation domes, the motion of the dental Layer 1425 acts as a barrier that separates the openings of layers 1424a and 1424b. Layers 1423a, 1423b, 1424a, 1424b, and 1425 may be manufactured from plastic, metals, or a mix of materials. For example, in some embodiments at least some of layers 1423a, 1423b, 1424a, 1424b, and 1425 may be formed by plastic that has been stamped into the appropriate shapes, while in other embodiments, the layers may be formed by plastic that has been molded. In other embodiments, at least some of layers 1423a, 1423b, 1424a, 1424b, and 1425 may be made from metal that has been stamped or chemically etched.

Layers 1423a, 1423b, 1424a, 1424b, and 1425 are stacked and laminated together to form the brush head 1322 as shown in view 1322b.

The activation domes are expanded and collapsed using the pump 1450 and the suction device 1460. According to some embodiments, two modes of operation can be employed: an in phase mode and an out of phase mode. In the in-phase mode of operation, the flexible domes are expanded and contracted in concert with one another so that all of the domes expand or collapse together. In the out-of-phase mode of operation, the at least a portion of the domes will expand while others are contracting.

According to some embodiments, a speaker-like unit 1422 is included in the brush handle portion 1310 of the device and is used to create short duration pressure increases that produce an undulating motion in the flexible domes. When bristle pads are coupled to the toothbrush head, the bristle tips can be made to move quickly yet not with great amplitude by employing pressure increases provided by the speaker-like unit 1422.

FIG. 20 illustrates a cross-section of a brush head 2122 for a power toothbrush that includes two dental arches 2002 and 2002 similar to dental arches 102 and 104 of brush head 122 described above. In the embodiment illustrated in FIG. 20, dental arches 2002 and 2004 are mirror images of one another, therefore, the description of the components of the upper dental arch 2004 apply to the similar components of lower dental arch 2002.

Side bladders 2050a and 2050b are coupled to the upwardly curving portions of the dental arch 2004. Side bladders 2050a and 2050b are inflated by pressure from the pump and cause a cleaning surface of the brush plate 2030 to contact the tooth surfaces, thereby causing the cleaning surface of the brush plate 2030 to conform to a user's teeth. Thus, the side bladders 2050a and 2050b perform a similar function as the flexible fingers of the various embodiments described above. According to some embodiments, a pulsed style pump is used instead of a pneumatic oscillator, which can reduce the cost and complexity of the power toothbrush. If the pressure and suction pulses are in opposite phase, then the pressure (P1) and suction (S1) can be directly connected together and fed into the brush head. With a manifold that connects P1 and S1 together, pressure phase difference between P1 and S1 results in bladder inflation and deflation, causing the brushes 2050a and 2050b to rise and fall rapidly. Pulse width modulation or phase delays can further provide ability to control brush amplitude and power.

According to some embodiments, the brush plate 2030 includes a stiff backing material against which the side bladders 2050a and 2050b apply pressure. According to some embodiments, the brush plate 2030 also includes hinges 2035a and 2035b that enable the brush plate to bend to form approximately a U-shape that engages multiple surfaces of tooth 2077. Actuator 2040 is inflated and deflated by the pump. As actuator 2040 inflates, the brush plate 2030 is forced upward along the tooth surfaces toward the gingival margin 2078. As actuator 2040 deflates, the brush plate 2030 is drawn downward along the tooth surface. The up and down motion of the brush plates causes the cleaning surfaces of the brush plates to scrub dental plaque from the tooth surfaces.

In some alternative embodiments, inflation and deflation of the flexible bladder 1560 causes the brush heads 2050a and 2050b to move in a side to side motion rather than an up and down motion.

FIG. 21 illustrates another view of brush head 2122 of FIG. 20 with the brush plates 2020 removed illustrate the positioning of the actuators 2040.

Figure 22:
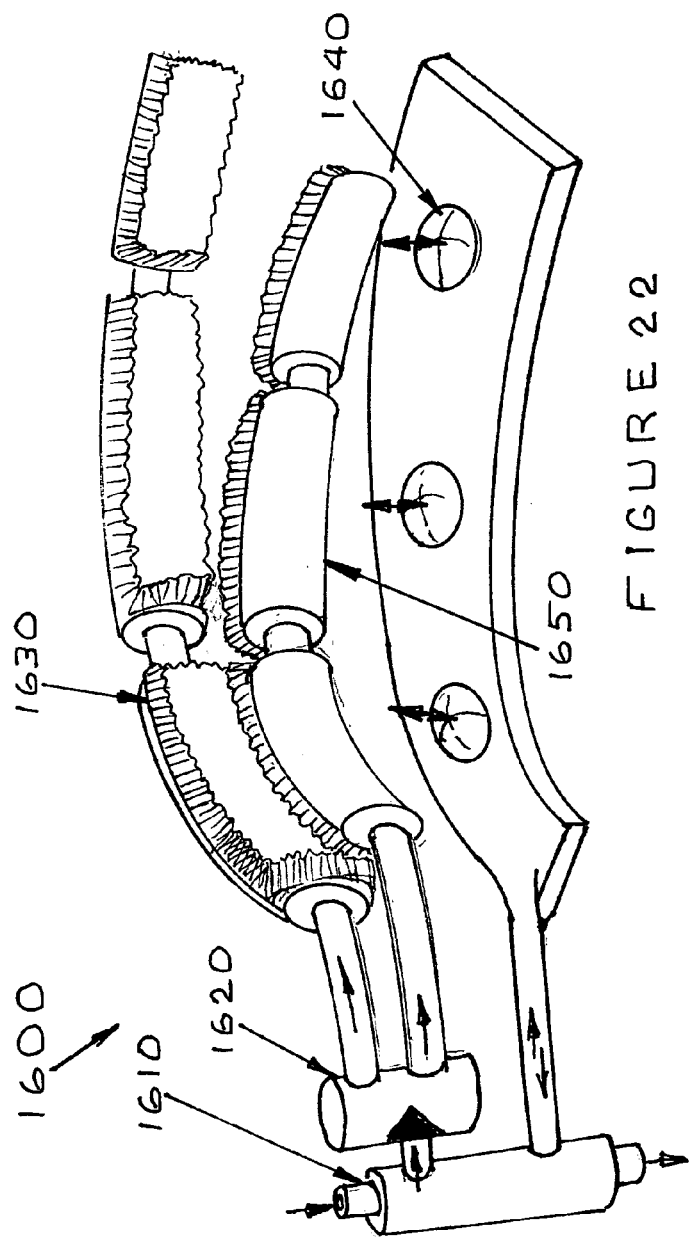
FIG. 22 illustrates a brush head for use with a power toothbrush.

FIG. 22 illustrates a brush head 1600 that may be used with a pulsed pressure pump, such as that described above with respect to FIGS. 17 and 18, according to an embodiment. Brush head 1600 includes a single dental arch configuration, the single dental arch of brush head 1600 may similar to dental arches 102 and 104 described above.

Pneumatic manifold 1610 enables the pulsed pump to pump air, gas, or fluid into side bladders 1650 and actuators 1640. The pneumatic manifold 1610 includes a one way pneumatic valve 1620 that prevents air from being removed from side bladders 1650 when the pump applies suction to the pneumatic manifold 1610. The out of phase pulsed pressure (P1) and suction (S1) enables the actuators to rise and fall rapidly. Side bladders 1650 receive a controlled amount of side pressure that is applied to the multiple brush plates 1630. According to some embodiments, the brush plates 1630 include a hinge or a flex seems that enable the brush plates to flex and engage the tooth surfaces when the side bladders 1650 are inflated. Actuators 1640 provide an up and down scrubbing action that causes the brush plates to clean the tooth surfaces.

FIG. 23 provides a cross-sectional view of the brush head illustrated in FIG. 22. The brush head is illustrated being used with a tooth 1777. Side bladders 1750a and 1750b are coupled to the upwardly curving portions of the dental arch 1715. Dental arch 1715 may be similar to dental arches 102 and 104 described above.

Side bladders 1750a and 1750b are inflated by pressure from the pump and cause a cleaning surface of the brush plate 1730 to contact the tooth surfaces, thereby causing the cleaning surface of the brush plate 1730 to conform to a user's teeth. Thus, the side bladders 1750a and 1750b perform a similar function as the flexible fingers of the various embodiments described above.

According to some embodiments, the brush plate 1730 includes a stiff backing material against which the side bladders 1750a and 1750b apply pressure. According to some embodiments, the brush plate 1730 also includes hinges 1735a and 1735b that enable the brush plate to bend to form approximately a U-shape that engages multiple surfaces of tooth 1777. Actuator 1740 is inflated and deflated by the pump. As actuator 1740 inflates, the brush plate 1730 is forced upward along the tooth surfaces toward the gingival margin 1778. As actuator 1740 deflates, the brush plate 1730 is drawn downward along the tooth surface. The up and down motion of the brush plates causes the cleaning surfaces of the brush plates to scrub dental plaque from the tooth surfaces.

Brush head 1600 is illustrated as including a single dental arch. Embodiments that include a single dental arch having a J-shape may be used to brush approximately a quarter of the mouth at once, and embodiments that include a U-shape may be used to brush approximately one half of the mouth at once. Either the maxillary or the mandibular dental arch may be brushed by simply flipping the brush over to orient the dental arch toward the teeth to be brushed. A single dental arch configuration, such as that illustrated in FIG. 20, is possible because the side bladders 1750a and 1750b and actuator 1740 have the relatively rigid surfaces of the dental arch 1715 and the brush plates 1730 to push against. Dental arch 1715 is held in a static position relative to the handle of the power toothbrush, while the brush plate 1730 are free to move as the side bladders 1750a and 1750b and actuator 1740 inflate and deflate thereby creating an up and down motion that mimics the brush motion of the Bass Method or Modified Bass Method.

According to some embodiments, brush head 122 described above could be similarly modified to operate with a single dental arch having a J-shape may be used to brush approximately a quarter of the mouth at once, and embodiments that include a U-shape may be used to brush approximately one half of the mouth at once. For example, dental arch 104 could be replaced with a rigid backing piece is held in a static position relative to the handle of the power toothbrush, and bladder 115 may be disposed between dental arch 102 and the rigid backing piece such that the inflation and deflation of bladder 115 drives dental arch 102 in an up and down motion fashion similar to that mimics the brush motion of the Bass Method or Modified Bass Method.

FIG. 24 illustrates an alternative embodiment of an actuator 1800. According to some embodiments, the actuators may include a spring that aids in the upward and downward motion of the actuator. Actuator 1800 includes a sealed, airtight upper portion 1810 forming a cavity in which spring 1820 is disposed. The upward force of spring 1820 causes the upper portion 1810 to rise upward. The cavity of actuator 1800 is also connected to manifold 1830. Manifold 1830 provides a sealed channel through which air or fluid can pass into the cavity of actuator 1800, the pressure of resulting from the addition of air or fluid to the cavity causing the upper portion 1810 to rise upward and the removal of air or fluid from the cavity causing the upper portion 1810 to move downward.

Spring 1820 provides additional upward force that may enable actuator 1800 to move in an upward direction more quickly than is possible solely through the addition of air or fluid to the cavity of actuator 1800. The pump generates sufficient suction force to remove air or fluid from the cavity to overcome the upward force imparted on upper portion 1810 by spring 1820.

According to some embodiments, a powered toothbrush includes spring actuators and a pump that only provides pulsed suction, the actuators lowering when suction is applied and rising due to the upward force of the springs when suction is not applied to the actuators.

Figure 25:
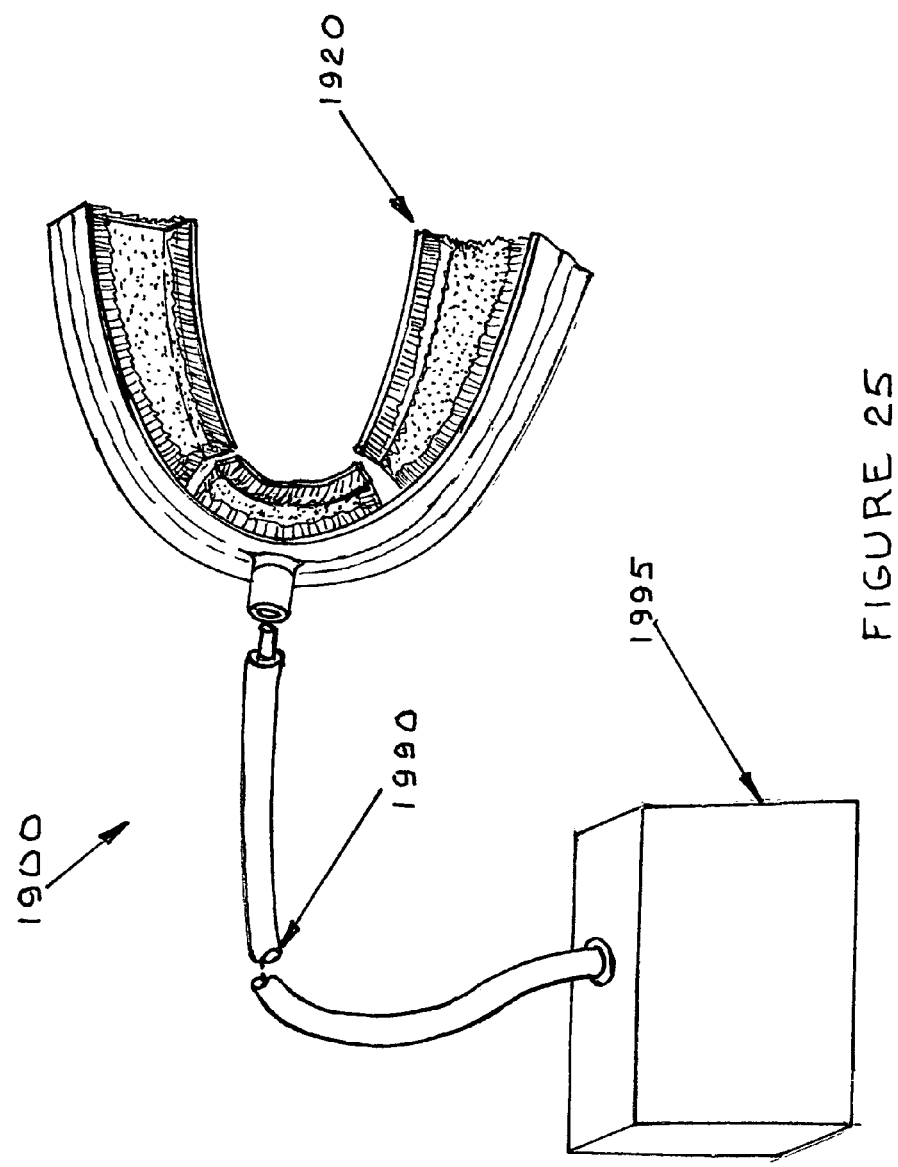
FIG. 25 illustrates a portable power toothbrush according to an embodiment.

FIG. 25 illustrates a power toothbrush 1900 according to an embodiment. Power toothbrush 1900 includes a brush head 1920, a power unit 1995, and a power cord 1990 that connects brush head 1920 to power unit 1995 and provides power to the brush head. According to some embodiments, brush head 1920 the driving mechanism includes several miniature wobble motors embedded in the brush head. The wobble motors, when powered, provide the bristle tip vibration and movement of the bristle pads against the tooth surfaces. The wobble motors are sealed to prevent water or other fluids from entering the motors while the brush head is being used or cleaned. According to some embodiments, brush head 1920 may be disconnected from power cord 1990 to enable the brush head to be cleaned and/or replaced.

Power unit 1995 includes a battery for powering the wobble motors and a power switch for turning the unit on or off. According to some embodiments, the battery is a disposable battery, while in other embodiments, the battery is a rechargeable battery. In embodiments where the battery is rechargeable, power unit 1995 includes a charging circuit for charging the batter using an external power source, such as mains power. According to some embodiments, power unit 1920 is enclosed in a watertight or water resistant case to prevent water or other fluids from entering the power unit during use of the power toothbrush.

In the embodiment illustrated in FIG. 25, brush head 1920 is a full-mouth brush designed to brush all of a user's teeth simultaneously. According to other embodiments, different brush designs may be used. For example, in some embodiments brush head 1920 is a half-mouth brush head, while in yet other embodiments, the brush head 1920 is a quarter-mouth brush head. According to some embodiments, the other pump variations described above with respect to pump 196 may be used to drive the brush heads instead of the wobble weight motors by coupling brush head 1920 to power unit 1995 through a length of air tubing coupled to a pump disposed in power unit 1995.

What is claimed is:

1. A power toothbrush comprising:
   a handle portion;
   a pneumatic device disposed within the handle portion; and
   a brush head coupled to the handle portion, the brush head comprising
   (a) a first dental arch including a first set of brush pads for simultaneously cleaning multiple tooth surfaces of a first set of teeth, the first set of teeth including at least one tooth from the maxillary dental arch of a user;
   (b) a second dental arch including a second set of brush pads for simultaneously cleaning multiple tooth surfaces of a second set of teeth, the second set of teeth opposing the first set of teeth, the second set of teeth including at least one tooth from the mandibular dental arch of the user;
   (c) an inflatable bladder disposed between the first and second dental arches, the inflatable bladder being in fluid communication with the pneumatic device, the pneumatic device providing pressure to inflate the bladder and suction to deflate the bladder.

2. The power toothbrush of claim 1 wherein the first and second dental arches are J-shaped, wherein the first set of teeth includes one half of the maxillary dental arch, and wherein the second set of teeth includes one half of the mandibular dental arch opposing the first set of teeth.

3. The power toothbrush of claim 1 wherein the first and second dental arches are U-shaped, wherein the first set of teeth includes all of the teeth of the maxillary dental arch of the user, and the second set of teeth includes all of the teeth of the mandibular arch.

4. The power toothbrush of claim 1 wherein the first dental arch includes at least one flex gap, the at least one flex gap enabling the first dental arch to flex longitudinally to conform to the maxillary arch of the user.

5. The power toothbrush of claim 1 wherein the second dental arch includes at least one flex gap, the at least one flex gap enabling the second dental arch to flex longitudinally to conform to the mandibular arch of the user.

6. The power toothbrush of claim 1 further comprising:
a first set of flexible fingers coupled to the first dental arch, the first set of flexible fingers applying pressure to the at least one brush pad so that a cleaning surface of the first set of brush pads maintains contact with the multiple tooth surfaces of the first set of teeth; and
a second set of flexible fingers coupled to the second dental arch, the second set of flexible fingers applying pressure to the at least one brush pad so that a cleaning surface of the second set of brush pads maintains contact with the multiple tooth surfaces of the second set of teeth.

7. The power toothbrush of claim 6 wherein the first and second set of flexible fingers comprise a low force flexible material.

8. The power toothbrush of claim 1 wherein the first and second set of brush pads include bristles set at an angle with respect to the surface of the teeth, where the angle ranges from an acute angle to a 90 degree angle, the bristles being directed toward the gingival sulcus.

9. The power toothbrush of claim 8 wherein the bristles of the first and second set brush pads are set at a 45 degree angle to the surface of the teeth.

10. The power toothbrush of claim 8 wherein the brush pads include bristles having multiple lengths.

11. The power toothbrush of claim 1 wherein the bladder is formed in a partly expanded condition and contains an internal rib to prevent complete wall collapse when pressure is applied to the brush head.

12. The power toothbrush of claim 1 wherein the brush head further comprises a bite guard that prevents the bladder from being fully collapsed.

13. The power toothbrush of claim 1 wherein the brush head is coupled to the handle portion with a coupling that may rotate up to 360 degrees.

14. A power toothbrush comprising:
a handle portion;
a brush head coupled to the handle portion, the brush head comprising
(a) an upper brush component for simultaneously cleaning multiple tooth surfaces of a first set of teeth;
(b) a lower brush component for simultaneously cleaning multiple tooth surfaces of a second set of teeth, the second set of teeth opposing the first set of teeth;
(c) a driving mechanism for driving the upper brush component and the lower brush component apart wherein the driving mechanism comprises a plurality of inflatable activation domes disposed between the upper and lower brush components, the inflatable activation domes being in fluid communication with a pneumatic pump, the pneumatic pump providing pressure to inflate the plurality of inflatable activation domes and suction to deflate the plurality of activation domes.

15. The power toothbrush of claim 14 wherein the plurality of inflatable activation domes each comprise a piston actuator, the piston actuator including a spring that applies an upward force that aids in the inflation of the inflatable activation domes.

16. A power toothbrush comprising: a handle portion; a brush head coupled to the handle portion, the brush head comprising (a) an upper brush component for simultaneously cleaning multiple tooth surfaces of a first set of teeth; (b) a lower brush component for simultaneously cleaning multiple tooth surfaces of a second set of teeth, the second set of teeth opposing the first set of teeth; (c) a driving mechanism for driving the upper brush component and the lower brush component apart wherein the driving mechanism comprises an inflatable bladder disposed between the upper and lower brush components, the inflatable bladder being in fluid communication with a pneumatic, the pneumatic pump providing pressure to inflate the bladder and suction to deflate the bladder.

17. A power toothbrush comprising: a handle portion; a brush head coupled to the handle portion, the brush head comprising (a) an upper brush component for simultaneously cleaning multiple tooth surfaces of a first set of teeth; (b) a lower brush component for simultaneously cleaning multiple tooth surfaces of a second set of teeth, the second set of teeth opposing the first set of teeth; (c) a driving mechanism for driving the upper brush component and the lower brush component apart wherein the driving mechanism comprises an inflatable double bladder disposed between the upper and lower brush components, the inflatable double bladder being in fluid communication with a pneumatic pump, the pneumatic pump providing pressure to inflate the bladder and suction to deflate the bladder.

18. A power toothbrush comprising: a handle portion; a brush head coupled to the handle portion, the brush head comprising (a) an upper brush component including a first set of brush pads for simultaneously cleaning multiple tooth surfaces of a first set of teeth; (b) a lower brush component including a second set of brush pads for simultaneously cleaning multiple tooth surfaces of a second set of teeth, the second set of teeth opposing the first set of teeth; (c) a driving mechanism for driving the upper brush component and the lower brush component apart wherein the brush head further comprises:
a first set of air bladders coupled to the upper brush component, the first set of air bladders being in fluid communication with a pneumatic pump via a manifold, the pneumatic pump providing pressure to inflate the first set of air bladders, wherein the first set of air bladders apply pressure to the first set of brush pads so that a cleaning surface of the first set of brush pads maintains contact with the multiple tooth surfaces of the first set of teeth; and
a second set of air bladders coupled to the lower brush component, the second set of air bladders being in fluid communication with the pneumatic pump via the manifold, the pneumatic pump providing pressure to inflate the second set of air bladders, wherein the second set of air bladders apply pressure to the second set of brush pads so that a cleaning surface of the second set of brush pads maintains contact with the multiple tooth surfaces of the second set of teeth.

19. The power toothbrush any one of claim 14, 16, 17 or 18 wherein the first set of teeth includes at least one tooth from the maxillary dental arch of a user, and wherein the second set of teeth includes at least one tooth from the mandibular dental arch of the user.

20. A method of brushing teeth using the power toothbrush of claim 1 which includes a brush head that includes a first dental arch and a second dental arch with a driving mechanism disposed between the first and second dental arches, the method comprising:

fitting the brush head to the mouth of a user such that the first dental arch conforms to a first set of teeth of the maxillary arch of the user and the second dental arch conforms to a second set of teeth of the mandibular arch of the user, the second set of teeth opposing the first set of teeth;

alternating between driving the first dental arch and the second dental arch together and driving the first dental arch and the second dental arch apart.

21. The method of claim 18 wherein alternating between driving the first dental arch and the second dental arch together and driving the first dental arch and the second dental arch apart further comprises:

driving the first dental arch and the second dental arch in a side to side motion in addition to the up and down motion.

* * * * *